(12) United States Patent
Walkenhorst et al.

(10) Patent No.: US 10,085,847 B2
(45) Date of Patent: Oct. 2, 2018

(54) MODULAR ANCHOR BONE FUSION CAGE

(71) Applicant: Zimmer Biomet Spine, Inc., Broomfield, CO (US)

(72) Inventors: Jared Walkenhorst, Denver, CO (US); Andrew Lamborne, Golden, CO (US); Allison Capote, Boulder, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 319 days.

(21) Appl. No.: 15/150,978

(22) Filed: May 10, 2016

(65) Prior Publication Data

US 2016/0324657 A1    Nov. 10, 2016

Related U.S. Application Data

(60) Division of application No. 13/841,932, filed on Mar. 15, 2013, now Pat. No. 9,364,342, which is a
(Continued)

(51) Int. Cl.
*A61F 2/44* (2006.01)
*A61B 17/70* (2006.01)
(Continued)

(52) U.S. Cl.
CPC ........ *A61F 2/4455* (2013.01); *A61B 17/7059* (2013.01); *A61F 2/447* (2013.01);
(Continued)

(58) Field of Classification Search
CPC .......... A61F 2/44; A61F 2/4455; A61F 2/446; A61F 2/4465; A61F 2/447
(Continued)

(56) References Cited

U.S. PATENT DOCUMENTS 6,306,139 B1 * 10/2001 Fuentes ............ A61B 17/1728
606/295
6,413,259 B1 * 7/2002 Lyons ................ A61B 17/8042
606/295
(Continued)

FOREIGN PATENT DOCUMENTS

CN    104203163 A    12/2014
CN    104203163 B    10/2016
(Continued)

OTHER PUBLICATIONS

"U.S. Appl. No. 13/841,932, Examiner Interview Summary dated Oct. 28, 2015", 3 pgs.
(Continued)

*Primary Examiner* — Eric S Gibson
(74) *Attorney, Agent, or Firm* — Schwegman Lundberg & Woessner, P.A.

(57) ABSTRACT

A modular anchor bone fusion cage is provided. The cage includes a spacer configured to fit into a space between the faces of two bones that are to be fused together. A fusion plate having at least a main body portion is coupled to the spacer. Fasteners extend through the fusion plate to engage the bone. At least some of the fasteners also extend through the spacer to engage the opposed faces of the bone. A cover plate is coupled to the fusion plate to inhibit the fasteners from backing out prior to fusion of the bones

21 Claims, 19 Drawing Sheets

Related U.S. Application Data continuation-in-part of application No. PCT/US2012/065912, filed on Nov. 19, 2012.

(60) Provisional application No. 61/561,119, filed on Nov. 17, 2011.

(51) Int. Cl.
*A61F 2/30* (2006.01)
*A61F 2/28* (2006.01)
*A61B 17/80* (2006.01)
*A61B 17/86* (2006.01)

(52) U.S. Cl.
CPC ........ *A61F 2/4465* (2013.01); *A61B 17/8047* (2013.01); *A61B 17/8645* (2013.01); *A61F 2/30744* (2013.01); *A61F 2002/2817* (2013.01); *A61F 2002/2835* (2013.01); *A61F 2002/3008* (2013.01); *A61F 2002/3023* (2013.01); *A61F 2002/3041* (2013.01); *A61F 2002/3051* (2013.01); *A61F 2002/3083* (2013.01); *A61F 2002/30375* (2013.01); *A61F 2002/30433* (2013.01); *A61F 2002/30439* (2013.01); *A61F 2002/30492* (2013.01); *A61F 2002/30497* (2013.01); *A61F 2002/30509* (2013.01); *A61F 2002/30517* (2013.01); *A61F 2002/30576* (2013.01); *A61F 2002/30578* (2013.01); *A61F 2002/30607* (2013.01); *A61F 2002/30616* (2013.01); *A61F 2002/30622* (2013.01); *A61F 2002/30777* (2013.01); *A61F 2002/30785* (2013.01); *A61F 2002/30787* (2013.01); *A61F 2002/30797* (2013.01); *A61F 2002/30835* (2013.01); *A61F 2002/30904* (2013.01); *A61F 2002/4475* (2013.01); *A61F 2220/0016* (2013.01); *A61F 2310/00017* (2013.01); *A61F 2310/00023* (2013.01); *A61F 2310/00071* (2013.01); *A61F 2310/00131* (2013.01); *A61F 2310/00161* (2013.01); *A61F 2310/00203* (2013.01); *A61F 2310/00239* (2013.01); *A61F 2310/00293* (2013.01); *A61F 2310/00329* (2013.01); *A61F 2310/00359* (2013.01)

(58) Field of Classification Search
USPC ................ 606/280–299; 623/17.16
See application file for complete search history.

(56) References Cited

U.S. PATENT DOCUMENTS

| | | | |
|---|---|---|---|
| 6,432,106 B1 | 8/2002 | Fraser | |
| 6,805,714 B2 | 10/2004 | Sutcliffe | |
| 7,112,222 B2 | 9/2006 | Fraser et al. | |
| 7,172,627 B2* | 2/2007 | Fiere | A61B 17/7059 623/17.11 |
| 7,819,903 B2 | 10/2010 | Fraser et al. | |
| 7,846,207 B2 | 12/2010 | Lechmann et al. | |
| 7,850,731 B2 | 12/2010 | Brittan et al. | |
| 7,862,616 B2* | 1/2011 | Lechmann | A61B 17/86 623/17.11 |
| 7,931,840 B2* | 4/2011 | Michelson | A61B 17/8605 264/162 |
| 8,216,312 B2* | 7/2012 | Gray | A61B 17/7059 606/249 |
| 8,540,774 B2* | 9/2013 | Kueenzi | A61F 2/4455 623/17.11 |
| 8,709,083 B2* | 4/2014 | Duffield | A61F 2/447 623/17.11 |
| 8,709,085 B2* | 4/2014 | Lechmann | A61B 17/86 623/17.11 |
| 8,715,354 B2* | 5/2014 | Lechmann | A61B 17/86 623/17.11 |
| 8,882,813 B2* | 11/2014 | Jones | A61B 17/7059 606/289 |
| 8,932,358 B1 | 1/2015 | Nehls | |
| 8,945,227 B2 | 2/2015 | Kirschman | |
| 9,005,295 B2* | 4/2015 | Kueenzi | A61F 2/4455 623/17.16 |
| 9,017,412 B2* | 4/2015 | Wolters | A61F 2/447 606/246 |
| 9,220,604 B2 | 12/2015 | Mcdonough et al. | |
| 9,220,609 B2 | 12/2015 | Mueller et al. | |
| 9,364,342 B2* | 6/2016 | Walkenhorst | A61B 17/7059 |
| 9,370,435 B2 | 6/2016 | Walkenhorst et al. | |
| 9,913,729 B2 | 3/2018 | Walkenhorst et al. | |
| 2002/0082597 A1 | 6/2002 | Fraser | |
| 2004/0210217 A1* | 10/2004 | Baynham | A61B 17/686 606/295 |
| 2005/0033433 A1 | 2/2005 | Michelson | |
| 2005/0085913 A1 | 4/2005 | Fraser et al. | |
| 2005/0101960 A1* | 5/2005 | Fiere | A61B 17/7059 623/17.11 |
| 2005/0177245 A1 | 8/2005 | Leatherbury et al. | |
| 2005/0216081 A1 | 9/2005 | Taylor et al. | |
| 2006/0030851 A1 | 2/2006 | Bray et al. | |
| 2006/0085071 A1* | 4/2006 | Lechmann | A61B 17/86 623/17.11 |
| 2006/0235533 A1* | 10/2006 | Blain | A61B 17/7059 623/17.16 |
| 2007/0173839 A1* | 7/2007 | Running | A61B 17/8042 606/86 B |
| 2007/0250167 A1 | 10/2007 | Bray et al. | |
| 2008/0161925 A1* | 7/2008 | Brittan | A61F 2/4465 623/17.16 |
| 2008/0294262 A1* | 11/2008 | Levieux | A61F 2/447 623/17.16 |
| 2008/0300634 A1 | 12/2008 | Gray | |
| 2008/0306596 A1* | 12/2008 | Jones | A61F 2/4455 623/17.16 |
| 2009/0012529 A1 | 1/2009 | Blain et al. | |
| 2009/0024171 A1 | 1/2009 | Leone | |
| 2009/0105830 A1* | 4/2009 | Jones | A61F 2/4455 623/17.16 |
| 2009/0105831 A1* | 4/2009 | Jones | A61B 17/7059 623/17.16 |
| 2009/0171396 A1* | 7/2009 | Baynham | A61B 17/686 606/280 |
| 2009/0182430 A1* | 7/2009 | Tyber | A61F 2/4465 623/17.16 |
| 2009/0210062 A1* | 8/2009 | Thalgott | A61F 2/4465 623/17.16 |
| 2009/0210064 A1* | 8/2009 | Lechmann | A61B 17/86 623/17.16 |
| 2009/0275988 A1 | 11/2009 | Baynham | |
| 2010/0137916 A1 | 6/2010 | Hynes et al. | |
| 2010/0145459 A1* | 6/2010 | McDonough | A61B 17/1728 623/17.16 |
| 2010/0145460 A1* | 6/2010 | McDonough | A61B 17/1728 623/17.16 |
| 2010/0217393 A1 | 8/2010 | Theofilos | |
| 2010/0249935 A1* | 9/2010 | Slivka | A61F 2/4465 623/17.16 |
| 2010/0249937 A1* | 9/2010 | Blain | A61B 17/7059 623/17.16 |
| 2010/0312345 A1* | 12/2010 | Duffield | A61F 2/4455 623/17.16 |
| 2011/0087327 A1* | 4/2011 | Lechmann | A61B 17/86 623/17.11 |
| 2011/0202136 A1* | 8/2011 | Brittan | A61F 2/4465 623/17.16 |
| 2012/0065734 A1* | 3/2012 | Barrett | A61F 2/4455 623/17.16 |
| 2012/0101580 A1* | 4/2012 | Lechmann | A61B 17/86 623/17.16 |
| 2012/0109308 A1* | 5/2012 | Lechmann | A61B 17/86 623/17.16 |
| 2012/0197401 A1 | 8/2012 | Duncan et al. | |

(56) References Cited

U.S. PATENT DOCUMENTS

| | | | |
|---|---|---|---|
| 2012/0232599 A1 | 9/2012 | Schoenly et al. | |
| 2012/0245690 A1* | 9/2012 | Cowan, Jr. | A61F 2/4465 623/17.16 |
| 2012/0277870 A1* | 11/2012 | Wolters | A61F 2/447 623/17.16 |
| 2012/0277873 A1* | 11/2012 | Kana | A61F 2/447 623/17.16 |
| 2013/0053895 A1* | 2/2013 | Stoll | A61B 17/8028 606/279 |
| 2013/0060337 A1* | 3/2013 | Petersheim | A61F 2/447 623/17.16 |
| 2013/0070344 A1 | 3/2013 | Gamache | |
| 2013/0073044 A1* | 3/2013 | Gamache | A61F 2/442 623/17.16 |
| 2013/0218276 A1* | 8/2013 | Fiechter | A61F 2/4455 623/17.16 |
| 2013/0238095 A1* | 9/2013 | Pavento | A61B 17/7059 623/17.16 |
| 2013/0268080 A1* | 10/2013 | Melkent | A61F 2/4455 623/17.16 |
| 2013/0345814 A1* | 12/2013 | Walkenhorst | A61F 2/4465 623/17.16 |
| 2014/0012380 A1* | 1/2014 | Laurence | A61F 2/4465 623/17.16 |
| 2014/0012384 A1* | 1/2014 | Kana | A61F 2/4465 623/17.16 |
| 2014/0039623 A1* | 2/2014 | Iott | A61F 2/30744 623/17.16 |
| 2014/0046447 A1* | 2/2014 | Dunworth | A61F 2/447 623/17.16 |
| 2014/0046448 A1* | 2/2014 | Kana | A61F 2/447 623/17.16 |
| 2014/0107785 A1* | 4/2014 | Geisler | A61F 2/442 623/17.16 |
| 2014/0107786 A1* | 4/2014 | Geisler | A61F 2/30965 623/17.16 |
| 2014/0114415 A1* | 4/2014 | Tyber | A61F 2/4455 623/17.16 |
| 2014/0180417 A1* | 6/2014 | Bergey | A61F 2/4455 623/17.16 |
| 2014/0180422 A1* | 6/2014 | Klimek | A61F 2/30744 623/17.16 |
| 2014/0200670 A1 | 7/2014 | Chin et al. | |
| 2014/0214166 A1* | 7/2014 | Theofilos | A61F 2/4455 623/17.16 |
| 2014/0214167 A1* | 7/2014 | Theofilos | A61F 2/4455 623/17.16 |
| 2014/0243985 A1* | 8/2014 | Lechmann | A61B 17/86 623/17.16 |
| 2014/0257487 A1* | 9/2014 | Lawson | A61F 2/4455 623/17.16 |
| 2014/0330386 A1* | 11/2014 | Walkenhorst | A61F 2/4465 623/17.16 |
| 2014/0336770 A1* | 11/2014 | Petersheim | A61F 2/4455 623/17.16 |
| 2014/0371859 A1* | 12/2014 | Petersheim | A61F 2/447 623/17.16 |
| 2015/0025635 A1* | 1/2015 | Laubert | A61F 2/447 623/17.16 |
| 2015/0190241 A1* | 7/2015 | Gowan | A61F 2/4455 623/17.16 |
| 2015/0216674 A1* | 8/2015 | Wolters | A61F 2/447 623/17.16 |
| 2015/0216675 A1* | 8/2015 | McDonough | A61B 17/1728 623/17.16 |
| 2016/0324657 A1* | 11/2016 | Walkenhorst | A61F 2/4465 |
| 2016/0338852 A1 | 11/2016 | Walkenhorst et al. | |

FOREIGN PATENT DOCUMENTS

| | | | | |
|---|---|---|---|---|
| WO | WO 2009064644 A1 * | 5/2009 | | A61F 2/44 |
| WO | WO-2009064644 A1 | 5/2009 | | |
| WO | WO-2011028306 A1 | 3/2011 | | |
| WO | WO-2013075124 A1 | 5/2013 | | |

OTHER PUBLICATIONS

"U.S. Appl. No. 13/841,932, Non Final Office Action dated Aug. 19, 2015", 19 pgs.

"U.S. Appl. No. 13/841,932, Notice of Allowance dated Feb. 10, 2016", 8 pgs.

"U.S. Appl. No. 13/841,932, Notice of Allowance dated Nov. 13, 2015", 8 pgs.

"U.S. Appl. No. 13/841,932, Response filed Jul. 29, 2015 to Restriction Requirement dated Apr. 29, 2015", 3 pgs.

"U.S. Appl. No. 13/841,932, Response filed Oct. 30, 2015 to Non Final Office Action dated Aug. 19, 2015", 14 pgs.

"U.S. Appl. No. 13/841,932, Restriction Requirement dated Apr. 29, 2015", 9 pgs.

"U.S. Appl. No. 14/359,070, Examiner Interview Summary dated Oct. 28, 2015", 3 pgs.

"U.S. Appl. No. 14/359,070, Non Final Office Action dated Aug. 19, 2015", 18 pgs.

"U.S. Appl. No. 14/359,070, Notice of Allowance dated Feb. 18, 2016", 7 pgs.

"U.S. Appl. No. 14/359,070, Notice of Allowance dated Dec. 2, 2015", 7 pgs.

"U.S. Appl. No. 14/359,070, Response filed Oct. 30, 2015 to Non Final Office Action dated Aug. 19, 2015", 12 pgs.

"U.S. Appl. No. 15/157,671, Preliminary Amendment filed Aug. 3, 2016", 8 pgs.

"Chinese Application Serial No. 201280067336.9, Office Action dated Apr. 5, 2016", W/ English Translation, 7 pgs.

"Chinese Application Serial No. 201280067336.9, Office Action dated Jul. 22, 2015", W/ English Translation, 17 pgs.

"Chinese Application Serial No. 201280067336.9, Response filed Dec. 1, 2015 to Office Action dated Jul. 22, 2015", W/ English Claims, 19 pgs.

"European Application Serial No. 12850227.5, Extended European Search Report dated Oct. 20, 2015", 7 pgs.

"European Application Serial No. 12850227.5, Noting of loss of rights mailed Feb. 20, 2015", 2 pgs.

"European Application Serial No. 12850227.5, Office Action dated Feb. 24, 2014", 3 pgs.

"European Serial Application No. 12850227.5, Communication pursuant to Rules 70(2) and 70a(2) filed Apr. 20, 2016", 14pgs.

"International Application Serial No. PCT/US2012/065912, International Preliminary Report on Patentability dated May 30, 2014", 13 pgs.

"International Application Serial No. PCT/US2012/065912, International Search Report dated Feb. 5, 2013", 2 pgs.

"International Application Serial No. PCT/US2012/065912 Written Opinion dated Feb. 5, 2013", 11 pgs.

"U.S. Appl. No. 15/157,671, Advisory Action dated May 25, 2017", 4 pgs.

"U.S. Appl. No. 5/157,671, Final Office Action dated Mar. 14, 2017", 13 pgs.

"U.S. Appl. No. 15/157,671, Non Final Office Action dated Jun. 12, 2017", 14 pgs.

"U.S. Appl. No. 15/157,671, Non Final Office Action dated Nov. 23, 2016", 17 pgs.

"U.S. Appl. No. 15/157,671, Notice of Allowance dated Oct. 25, 2017", 8 pgs.

"U.S. Appl. No. 15/157,671, Response filed Feb. 22, 2017 to Non Final Office Action dated Nov. 23, 2016", 11 pgs.

(56) References Cited

OTHER PUBLICATIONS

"U.S. Appl. No. 15/157,671, Response filed May 15, 2017 to Final Office Action dated Mar. 14, 2017", 11 pgs.
"U.S. Appl. No. 15/157,671, Response Filed Jun. 2, 2017 to Advisory Action dated May 25, 2017", 11 pgs.
"U.S. Appl. No. 15/157,671, Response filed Sep. 12, 2017 to Non Final Office Action dated Jun. 12, 2017", 11 pgs.
"U.S. Appl. No. 15/884,452, Non Final Office Action dated Mar. 1, 2018", 13 pgs.

* cited by examiner

MODULAR ANCHOR BONE FUSION CAGE

CROSS REFERENCE TO RELATED APPLICATIONS

This application is a Continuation-In-Part of International Patent Application No. PCT/US12/65912 titled "Modular Anchor Bone Fusion Cage," filed on Nov. 19, 2012, which claims priority to U.S. Provisional Patent Application No. 61/561,119 titled "Modular Anchor Bone Fusion Cage," filed on Nov. 17, 2011. The entire disclosure of each of these applications is incorporated herein by reference.

BACKGROUND

The human spine contains a series of bony segments separated by discs and coupled together with muscle, ligaments, and other connective tissues. A large number of ailments may afflict one or more of these components. One exemplary ailment generally occurs with age as the spinal discs begin to break down, or degenerate resulting in the loss of fluid in the discs, and consequently, the discs become less flexible. Likewise, the discs become thinner allowing the vertebrae to move closer together. Degeneration also may result in tears or cracks in the outer layer, or annulus, of the disc. Degeneration of the annulus may allow the disc to begin to bulge outwardly. In more severe cases, the inner material of the disc, or nucleus, may extrude out of the disc. In addition to degenerative changes in the disc, the spine may undergo changes due to trauma from automobile accidents, falls, lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions, as well as others not specifically mentioned, are collectively referred to herein as spine disease.

Conventionally, surgeons treat spine disease by attempting to restore the normal spacing between adjacent vertebrae. This may be sufficient to relieve pressure from affected nerve tissue. However, it is often necessary to surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Although techniques for placing intervertebral spacers, plates, and pedicle screw fixation systems have become less invasive in recent years, they still require the placement of hardware deep within the surgical site adjacent to the spine. The hardware is frequently related to the intervertebral spacer, itself, along with additional hardware to immobilize the vertebral segment associated with the fusion. The additional hardware also inhibits the spacer from exiting the space. Recovery from such surgery can require several days of hospitalization and long, slow rehabilitation to normal activity levels.

Thus, it would be desirable to provide an implantable intervertebral spacer that presented as low a profile as possible while still providing sufficient hardware to facilitate immobilizing the vertebral segment being fused.

SUMMARY

This Summary is provided to a selection of concepts in a simplified and incomplete manner highlighting some of the aspects further described in the Detailed Description. This Summary, and the foregoing Background, is not intended to identify key aspects of essential aspects of the claimed subject matter. Moreover, this Summary is not intended for use as an aid in determining the scope of the claimed subject matter.

In some aspects of the technology disclosed by the present application, an implant is provided. The implant generally relates to fusing two honey segments together using as low a profile as possible. In one aspect of the technology, the implant has a spacer and a fusion plate that may be coupled to the spacer. The spacer is configured to fit between the two honey segments and promote fusion therebetween. The fusion plate couples to a rear (sometimes an anterior) portion of the spacer. The fusion plate includes a main body portion generally conforming in size and shape to the rear portion of the spacer and a first extension side extending from the main body portion of the fusion plate to overlie a portion of the bones to be fused together. The implant is coupled by fasteners extending through the fusion plate. Some of the fasteners may intersect with the rear portion of the spacer and extend through the top or bottom portion of the spacer. Some of the fasteners may extend through the fusion plate directly into the bone, although a portion of the fastener may intersect with the rear portion of the spacer.

In another aspect of the technology, the implant may include a spacer and a fusion plate that is coupled to the spacer. The spacer includes a forward (or posterior) portion and two arm portions that extend in the rearward (or anterior) direction. The arms may include an indentation on a lateral side. The fusion plate may include a hook coupled to a lock tab that cooperatively engages the indentation to form a snap-lock between the spacer and the fusion plate.

In still other aspects of the technology provided by the present application a cover plate may further be provided. The cover plate may be coupled to the fusion plate to inhibit the fasteners from reverse threading to promote the immobilization of the honey segment.

In certain embodiments, the spacer will be provided with a cavity where the main body portion of the fusion plate fits within the cavity to allow a portion of the fusion plate to reside in the space between the honey segments. In these embodiments, the first extension side will angle or flare from the main body portion of the fusion plate to allow the first extension side to reside along one of the adjacent bones. The first extension side may be straight, curved, sinusoidal, or a combination thereof.

In certain embodiments provided by the technology of the present application, the spacer will have a spacer bore that is coupled to a first end of a connector. In certain aspects, the spacer bore will have a thread that cooperatively engages an external thread of the connector, such as, for example, a set screw. The fusion plate will correspondingly have an aligned plate bore that is coupled to a second end of the connector. In certain aspects, the plate bore will have a shoulder and the second end of the connector will have a plurality of protrusions with outturned lips. The second end will be elastically deformable to form a snap fit between the outturned lips of the second end of the connector and the shoulder of the plate bore. In certain aspects a cover plate will further have a cover plate bore with a thread. The cover plate bore aligns with the plate bore. A connecting pin couples the cover plate to the fusion plate. In certain aspects of the technology, the connecting pin has a head and a shaft. The shaft has a first thread proximate to the head and a second thread distal to the head. An intermediate portion of the shaft may be non-threaded to separate the first thread from the second thread. The second thread may cooperatively engage an internal thread of the connector and the first thread may cooperatively engage the thread of the cover plate bore to couple the cover plate to the fusion plate.

This summary provides only a general outline of some aspects of the technology disclosed herein. The above and other aspects of the technology of the present application will be apparent after consideration of the Detailed Description and Figures herein. It is to be understood, however, that the scope of the application shall be determined by the claims as issued and not by whether given subject matter addresses any or all issues noted in the Background or includes any features or aspects highlighted in the Summary,

BRIEF DESCRIPTION OF THE DRAWINGS

Various examples of the present invention will be discussed with reference to the appended drawings. These drawings depict only illustrative examples of the invention and are not to be considered limiting of its scope.

DETAILED DESCRIPTION

The technology of the present patent application will now be explained with reference to various figures and the like. While the technology of the present application is described with respect to implants that facilitate spinal fusion, such as, for example, anterior lumbar interbody fusion (ALIF) implants, one of ordinary skill in the art would recognize on reading the disclosure that the technology is applicable to other implants. For example, the technology as described herein may be used for implants to facilitate fusion of other spinal fusions, such as a transforaminat lumbar interbody fusion (TLIF), anterior cervical discectomy (ACD), posterior lumbar interbody fusion (PLIF), lateral thoracolumbar fusions, and other skeletal fusions, such as long bones or the like. Moreover, the technology of the present patent application will be described with reference to certain exemplary embodiments herein. The word "exemplary" is used herein to mean "serving as an example, instance, or illustration." Any embodiment described herein as "exemplary" is not necessarily to be construed as preferred or advantageous over other embodiments or examples absent a specific indication that such an embodiment or example is preferred or advantageous over other embodiments. Moreover, in certain instances, only a single "exemplary" embodiment is provided. A single example is not necessarily to be construed as the only embodiment. The detailed description includes specific details for the purpose of providing a thorough understanding of the technology of the present patent application. However, on reading the disclosure, it be apparent to those skilled in the art that the technology of the present patent application may be practiced with or without these specific details. In some descriptions herein, generally understood structures and devices may be shown in diagrams to aid in understanding the technology of the present patent application without obscuring the technology herein.

Figure 1:
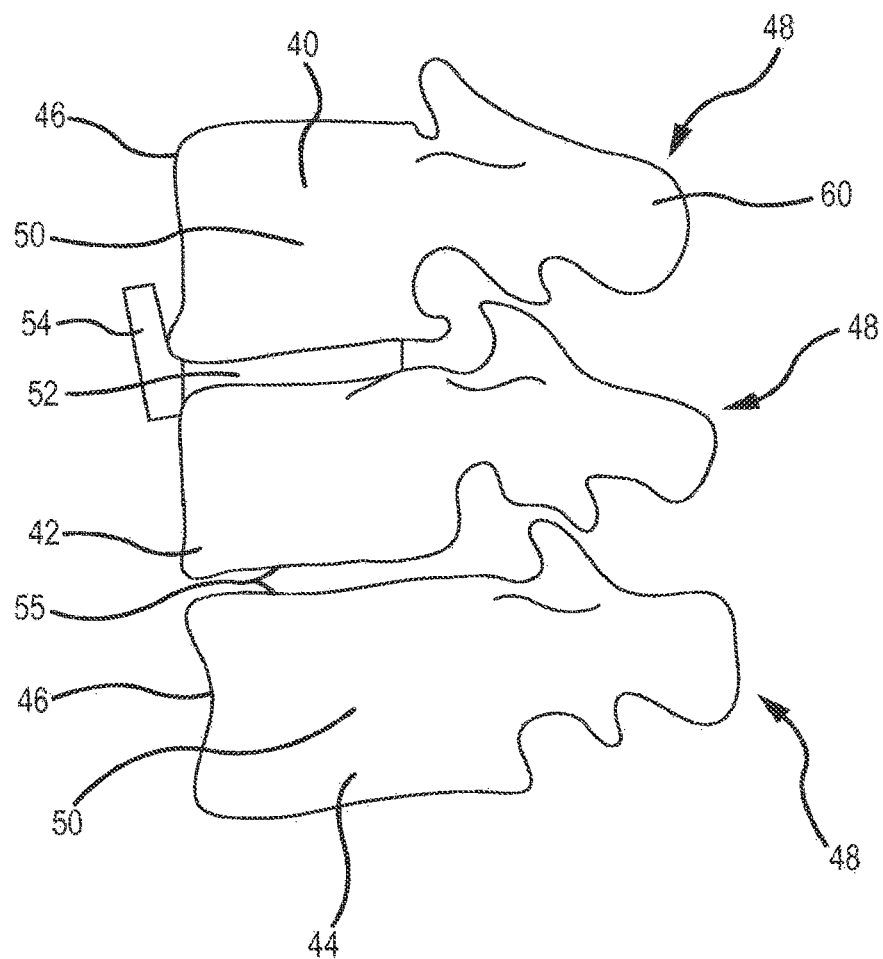
FIG. 1 is a side view of three adjacent vertebra having an implant consistent with the technology of the present application.

Referring first to FIG. 1, three vertebrae 40, 42, and 44 are provided. Each of the vertebrae 40, 42, and 44 have an anterior side 46, a posterior side 48 and lateral sides 50 (only one shown). The three vertebrae 40, 42, and 44 each have a spinous process 60.

In a normal spine, discs would reside between each of the endplates 55 of vertebrae 40 and 42, and vertebrae 42 and 44. The endplates 55 form opposed bony surfaces for spinal application, but use of the technology to be described herein is applicable to any bony segments to be fused across opposed facing bony surfaces. For convenience of illustration, the discs are not included in the figures. However, injury, age, disease, or other trauma may cause the discs to degenerate for one reason or another. To restore proper height to a disc, for example, a surgeon would remove all or a portion of the disc and replace it with a spacer. For example, as shown in FIG. 1, a spacer 52 may be surgically implanted in the space between vertebrae 40 and 42. As shown, spacer 52 is implanted from the anterior side of the patient. A fusion plate 54, as will be explained further below, is coupled to the spacer 52 and extends over only one of the vertebrae 40 and 42 in the exemplary embodiment of the technology shown in FIG. 1. While shown in a spinal application, the technology of the present application is usable to facilitate the fusion of other bones.

Figure 2:
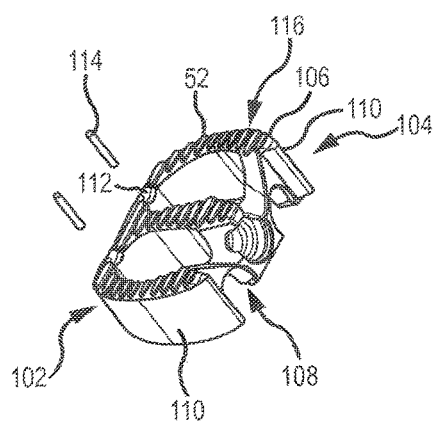
FIG. 2 is perspective view of a spacer consistent with the technology of the present application.
Figure 3:
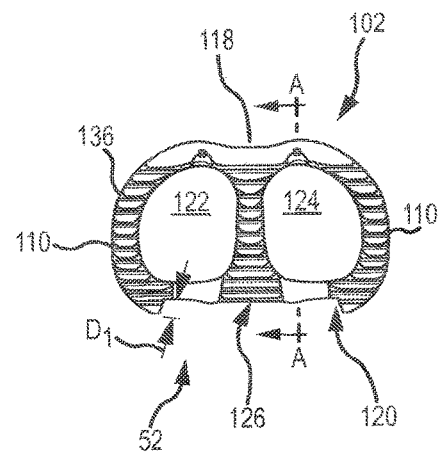
FIG. 3 is a top plan view of the spacer of FIG. 2.

Referring now to FIGS. 2 and 3, an exemplary spacer 52 is shown. The spacer 52 is generally shaped to fit within the intervertebral space and has a forward portion 102, which may be referred to as a posterior portion 102, a rearward portion 104, which may be referred to as an anterior portion 104, a top portion 106, which may be referred to as a superior portion 106, a bottom portion 108, which may be referred to as an inferior portion 108, and side portions 110. The spacer 52 may have apertures 112 to receive radio opaque plugs 114, which are useful for tracking when using computer assisted surgery, and as marking for fluoroscopy or other imaging techniques in which the bulk of spacer 52 may be difficult to visualize. The orientation of the front (posterior), rear (anterior), left, right, top (superior), and bottom (inferior), or the like are provided for reference and should not be construed to limit the technology of the present application. The spacer 52 is provided to fit entirely in the intervertebral space; although in certain embodiments, the rearward portion 104 may extend beyond the anterior ends of the vertebrae.

As shown in FIG. 3, the forward portion 102 is shaped to have a convex, concave, and convex portion forming a recess 118. The recess 118 is configured to avoid the dura in spinal applications, but would not be necessary for other applications of the technology. The rearward portion 104 is generally shaped to have a convex shape consistent with the anterior aspect of the vertebrae 40, 42 between which it is implanted. The rearward portion 10.4 comprises a cavity 120 having a depth $D_1$ to receive a fusion plate as will be explained further below. The side portions 110 provide a convex portion transitioning between the forward portion 102 and the rearward portion 104. The spacer 52, as shown, has a first and a second void 122, 124 separated by a central strut 126 providing the spacer 52 with a vaguely "B" shape.

Other shapes and types of spacers 52 are possible, such as, for example, other fusion cages, dowels, and the like. The first void 122 and second void 124 may be packed with material to facilitate bone growth and fusion of the vertebrae 40, 42. The first and second voids 122, 124 are both generally greater than 20% of the surface area of the spacer 52. Alternatively to the large first and second voids 122, 124, a large number of smaller bone growth channels are possible.

Figure 4:
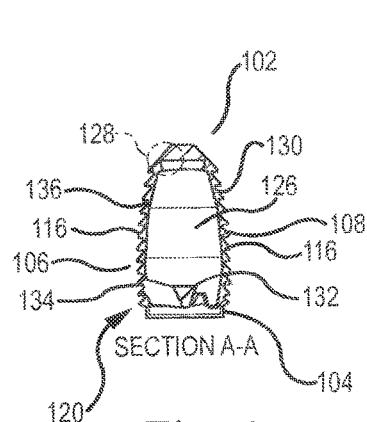
FIG. 4 is a cross-sectional view along line A-A of FIG. 3.

A number of protrusions 116 may be provided on the top portion 106, the bottom portion 108, or a combination thereof. As best seen in FIG. 4, which is a cross-sectional view across line A-A in FIG. 3, the protrusions 116 form a generally shark-tooth shape that angles from the forward portion 102 towards the rearward portion 104. The protrusions 116 generally resist movement of the spacer 52 out of the intervertebral space between vertebrae 40, 42. As shown in the cross-section, the top portion 106 and bottom portion 108 may be convex shapes providing the spacer 52 with a bi-convex shape from the forward portion 102 to the rearward portion 104 forming a dome shape close to a lordotic curvature or positioning of the vertebrae. The forward portion 102 (or posterior portion 102) has a taper 128 to facilitate insertion of the spacer 52. The forward portion 102 expands symmetrically on both sides to a thicker section. The spacer 52, in this exemplary embodiment, is generally thickest in the rearward portion 104, but generally forward of cavity 120. Instead of a bi-convex, domed shape, the spacer 52 may form a more conventional wedge shape or have a planar top portion 106, a planar bottom portion 108, or a combination thereof.

Still with reference to FIG. 4, the protrusions 116 are formed by a first surface 130 forming an obtuse angle with a surface of the spacer 51 The first surface 130 extends to an engaging surface 132 of the protrusion 116. The engaging surface 132 is adapted to engage the endplates 55 of the vertebrae 40, 42. The engaging surface 132 may be formed to a line contact, a point contact, or to a flat or convex surface formed generally parallel to the body surface. In particular, the engaging surface 132 may be formed and shaped to conform to the anatomical shape of the associated endplates. A surface formed by connecting the engaging surface 132 on the top and bottom portion 106, 108, may be shaped to conform to the anatomical shape of the associated endplates as well. A second surface 134 extends from the engaging surface 132 back to the surface of the spacer 52. The second surface 134 also forms an obtuse angle, but may form a right angle or be slightly undercut. The protrusions 116 are generally of a unified construction with the body. The protrusions 116 are separated by a flat or scooped gap 136 between each protrusion and generally extend over the entire superior and inferior surface of the implant. However, the forward portion 102 has a portion without protrusions, generally associated with the taper 128. In a particular embodiment, protrusions 116 have a shape as generally disclosed in U.S. Pat. Nos. 7,041,137 or 7,427,294, both of which are assigned to the assignee of the present application and the complete disclosures of which are incorporated herein by reference for all purposes.

Figure 5:
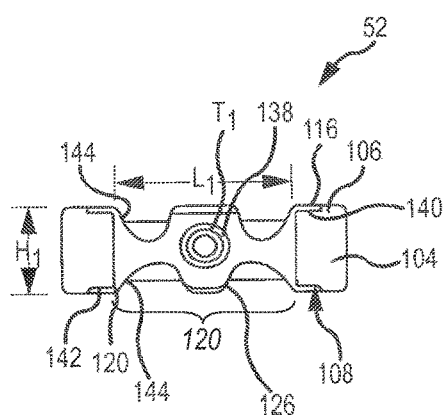
FIG. 5 is rearward portion elevation view of the spacer of FIG. 2.

Referring now to FIG. 5, an elevation view of the rearward portion 104 of spacer 52 is provided. Cavity 120 has a length $L_1$ and a height and is sized to cooperatively engage a fusion plate, which will be explained further below. A threaded spacer bore 138 is in the cavity 120. The threaded spacer bore 138 is used, as will be explained further below, to couple the spacer 52 and the fusion plate. The threaded spacer bore 138 may have an undercut. The threaded spacer bore 138 extends into the central strut 126. The threaded spacer bore 138 has a first thread $T_1$. The cavity 120 has an upper edge 140 at a transition to the top portion 106 and a lower edge 142 at a transition to the bottom portion 108. A spacer channel 144 is accessible from cavity 120 and exists in each of the upper edge 140 and the lower edge 142. As shown, there are two spacer channels 144 proximate the upper edge 140 and two spacer channels 144 proximate the lower edge 142. The spacer channels 144 are shown as having generally half-cylindrical shapes, such as a half pipe, U shapes, or V shapes that provides a guide for a fastener, which will be explained further below. The spacer channels 144 may be bores as well. The spacer channels 144 are shown on both the upper and lower edge 140, 142 of the spacer 52. In certain aspects of the technology, the spacer channels 144 may only be oriented on the upper edge 140 or the lower edge 142.

As can be appreciated on reading the above, the spacer 52 is provided with a length $L_2$ and a height $H_1$ to provide an implant having a reasonably low profile to fit within the intervertebral space with the spacing desired by the surgeon. To anchor the spacer 52 to the superior and inferior vertebrae, a fusion plate 54 (FIG. 1) is provided in certain aspects of the technology of the present application. In many embodiments, the plate provided has as low a profile as possible.

Figure 6:
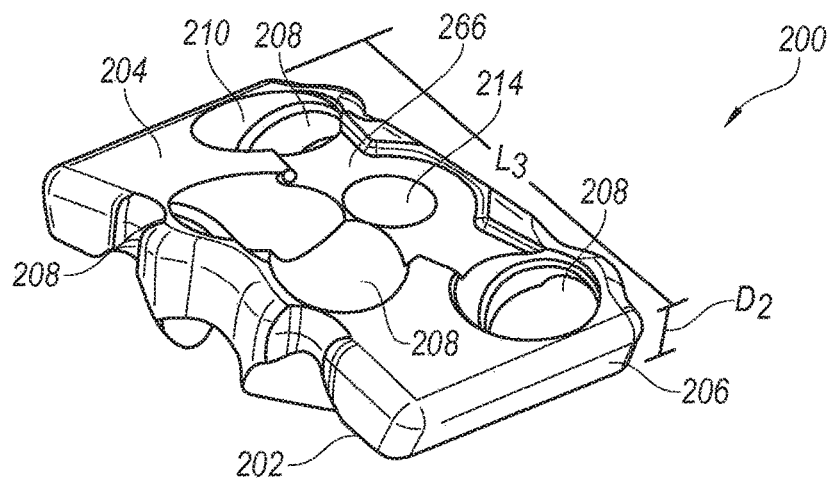
FIG. 6 is a perspective view of a fusion plate consistent with the technology of the present application.
Figure 7:
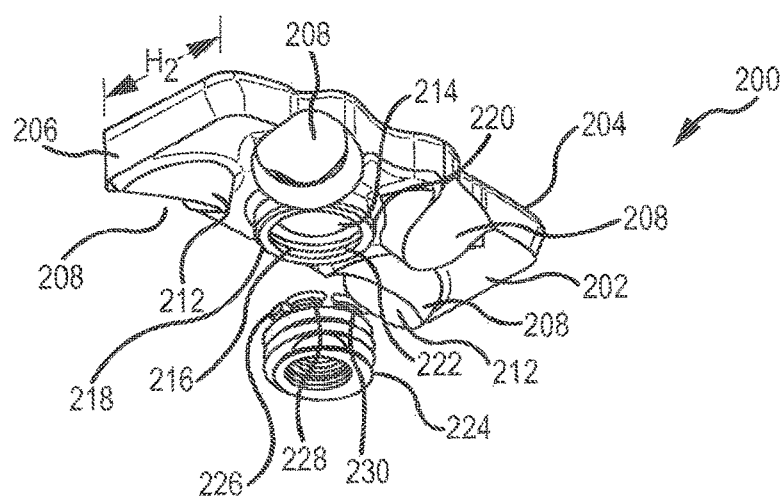
FIG. 7 is another perspective view of the fusion plate of FIG. 6.

Referring now to FIGS. 6 and 7, a low profile fusion plate 200 consistent with the technology of the present application is provided. The low profile fusion plate 200 has a forward face 202 and a rearward face 204 opposite the forward face 202. A sidewall 206 extends between the forward face 202 and the rearward face 204. The edges of sidewall 206 may be beveled or chamfered to reduce trauma. The low profile fusion plate 200 has a length $L_3$, a height $H_2$, and a depth $D_2$ to allow low profile fusion plate 200 to cooperatively engage cavity 120. The low profile fusion plate 200 has a plurality of fastener bores 208 that generally correspond to the spacer channels 144 associated with the spacer 52. The fastener bores 208 have an internal sidewall 210 forming a concave surface for cooperative engagement with a fastener as will be described below. In some embodiments, the concave surface formed by internal sidewall 210 generally is a spherical shape or curvature. The forward face 202 may have a plurality of protrusions 212 extending therefrom to cooperatively engage the spacer channels 144. As shown, the protrusions 212 are generally shaped as partial cylindrical surfaces.

The low profile fusion plate 200 further comprises a plate bore 214. The plate bore 214 is adapted to be aligned with threaded spacer bore 138. The plate bore 214 has an inner wall 216 and an outer wall 218 (shown in FIG. 7) extending from forward face 202 into threaded spacer bore 138. The plate bore 214 at a distal end thereof may have an outwardly turned lip 220. The plate bore 214 may be fitted to the spacer 52 by causing outwardly turned lip 220 to engage the undercut in the threaded spacer bore 138, as described above. Moreover, the inner wall 216 may be provided with a shoulder 222, which may be a ledge extending into the bore or a groove extending into the wall.

Figure 8:
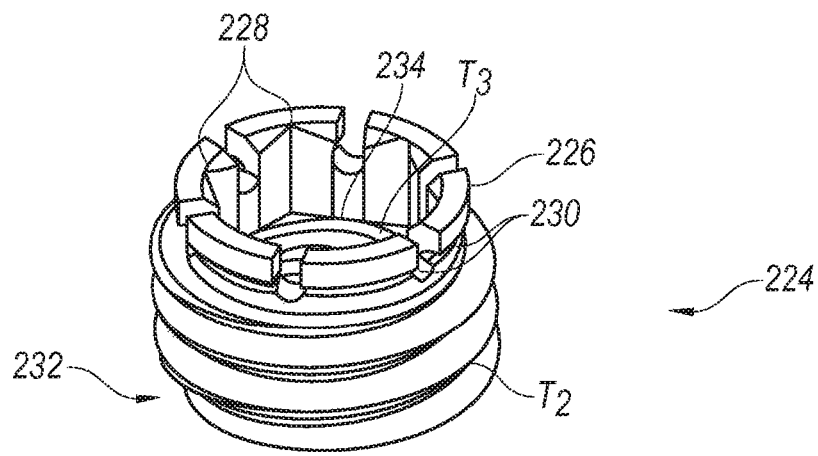
FIG. 8 is perspective view of a threaded connector shown in FIG. 7 consistent with the technology of the present application.

In one aspect of the technology, the low profile fusion plate 200 is coupled to the spacer 52 using a threaded connector 224 as shown in FIGS. 7 and 8. The threaded connector 224 has a slotted head end 226. The slots form a number of compressible protrusions 228 with outwardly turned lips 230. The threaded connector 224 also has a threaded shaft 232. The threaded shaft 232 has an outer thread $T_2$ adapted to cooperatively engage the threads $T_1$ of threaded spacer bore 138. The threaded connector 224 also comprises an inner threaded bore 234 having inner threads $T_3$ as will be explained further below.

The threaded connector 224 is coupled to the low profile fusion plate 200 by inserting the slotted head end 226 of the threaded connector 224 into the plate bore 214. The head end compresses until the outwardly turned lips 230 extend past the shoulder 222, at which point the slotted head expands to form a snap lock between the threaded connector 224 and the low profile fusion plate 200. In alternative embodiments, the threaded connector 224 is coupled to the fusion plate 200 with a C-ring, a split ring, or the like. The threaded connector 224 also is threaded into the threaded spacer bore 138 to couple the low profile plate to the spacer 52.

Figure 9:
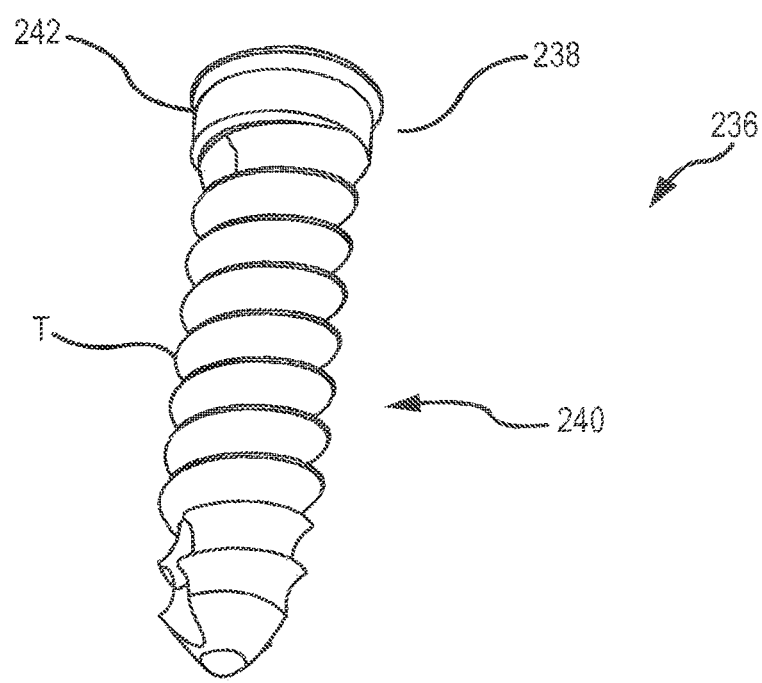
FIG. 9 is perspective view of a fastener consistent with the technology of the present application.

The spacer 52 and the low profile fusion plate 200 are coupled to the superior and inferior vertebrae in this exemplary aspect by a plurality of fasteners 236. The fasteners 236 may be any conventional fasteners, such as, for example, a bone screw 236 as shown in FIG. 9. The bone screw 236 may comprise a head 238 and a shaft 240 having threads T. The head 238 may be provided with a convex lower surface 242 to cooperatively engage the internal sidewall 210 of the fastener bores 208 in the low profile fusion plate 200. The fasteners 236 are adapted to be threaded into the endplates of the vertebrae 40, 42 by extending from the fastener bores into the rearward portion 104 of the spacer 52 and out of at least one of the top portion 106 or bottom portion 108.

Figure 10:
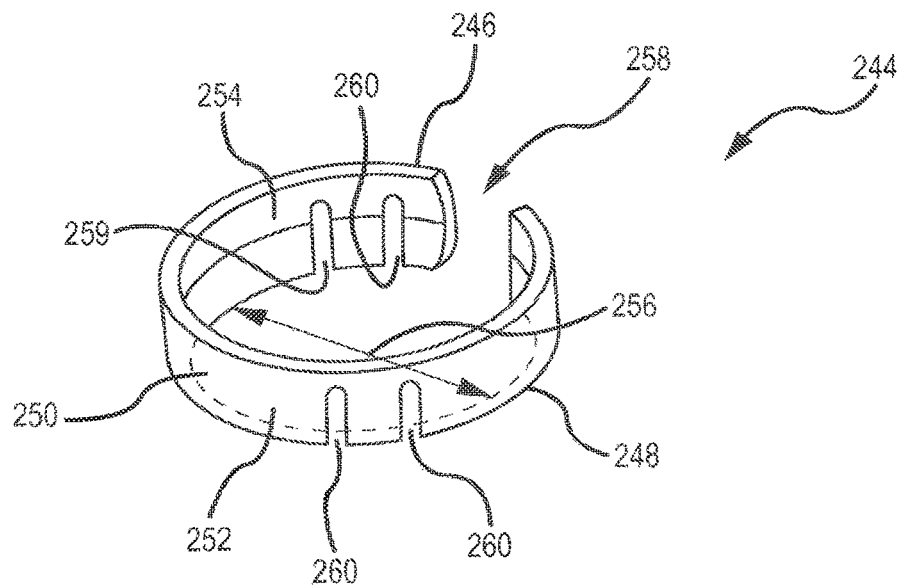
FIG. 10 is a perspective view of a lock usable with the technology of the present application.

The fasteners 236, as is conventionally known, may have a tendency to reverse thread or back-out of the vertebrae 40, 42, the spacer 52, and the fusion plate 54. A lock may be provided to inhibit the fasteners 236 from reverse threading. In certain aspects of the technology, the lock is similar to bushing 244 as shown in FIG. 10. The bushing 244 comprises a top edge 246, a bottom edge 248, and a bushing wall 250 extending between the top and bottom edges 246, 248. The bushing sidewall 250 would have an outer surface 252 to cooperatively engage internal sidewall 210 of the fusion plate 54 and an inner surface 254 to cooperatively engage the convex lower surface 242 of the head 238 of the fastener 236. The diameter 256 of the bushing may vary from the top edge 246 to the bottom edge 248.

As shown, in this exemplary embodiment, the bushing is generally cylindrical in shape, but other shapes are possible. The bushing 244 would have a diameter consistent with the diameter of the plate bore 214 and fit between the head 238 of the fastener 236 and the internal sidewall 210 of the plate bore 214. As is conventionally known, the bushing 244 may have a gap 258 to allow the bushing 244 to be compressed and fitted into plate bore 214. Moreover, the bushing 244 may have a number of slots 259 shown in the bottom portion of the bushing 244, which could be in the top portion of bushing 244 or a combination thereof as well. The slots 260 allow portions of the bushing 244 to flex to facilitate implanting the fasteners 236. The bushing 244, as a fastener lock, helps secure fastener 236 to plate 54.

Figure 11:
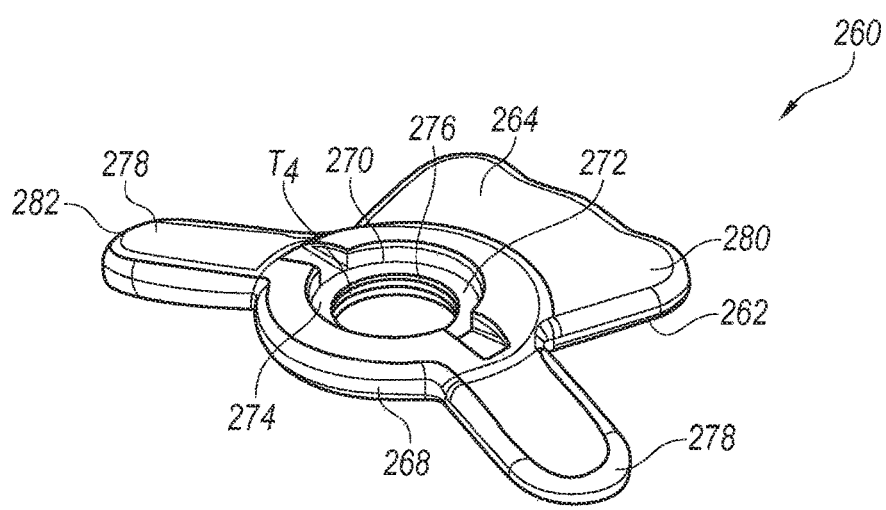
FIG. 11 is a perspective view of a cover plate consistent with the technology of the present application.

Alternatively to bushings, the lock may be a cover plate. Referring now to FIG. 11, a cover plate 260 is provided that is usable with the low profile fusion plate 200. The cover plate 260 has a first face 262 and a second face 264 opposite the first face 262. The cover plate 260 may be shaped to fit into a recess 266 in the low profile fusion plate 200, as shown in FIG. 6. The cover plate 260, as shown, generally has a main body portion 268 with a cover plate bore 270, which is shown with a countersunk region 272. The cover plate bore 270 includes a shoulder 274 separating a threaded portion 276 having threads $T_4$ of the cover plate bore 276 from a non-threaded portion.

A connecting pin, which will be explained further below, couples the cover plate 260 to the low profile fusion plate 200. The cover plate bore 270 aligns with the plate bore 214 described above. A plurality of arms 278 or flared extensions 280 extend from the main body portion 268. The arms 278 extend from the main body portion a sufficient distance such that at least a distal end 282 of the arm extends over fastener bore 208. The distal end 282 of the arm, thus, resists the ability of the fastener 236 to reverse thread from the implant. The flared extension(s) 280 extends from the main body portion a sufficient distance such that at least a distal end 282 of the flared extension(s) 280 extends over one or more fastener bores 208. The distal end 282 of the extension, thus, resists the ability of the fastener 236 to reverse thread from the implant.

As can be appreciated, the shape, size, and whether arms or flared extensions are associated with cover plate 260 depends in part on the shape and size of fusion plate 54 (shown in FIG. 1). The shape and size of the cover plate 260 specifically shown in FIG. 11 is designed for use with the low profile fluxion plate 200 shown in FIGS. 6 and 7. Generally, arms on cover plate 260 are associated with a single fastener bore 208 and flared extension(s) 280 are associated with multiple fastener bores 208.

Figure 12:
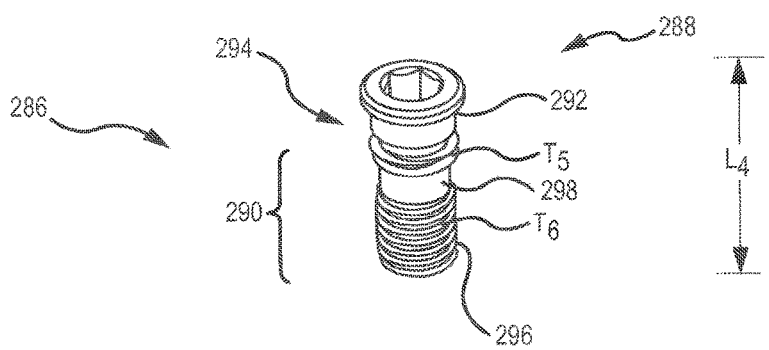
FIG. 12 is perspective view of a connector pin consistent with the technology of the present application.

As described above, the cover plate bore 270 generally aligns with the plate bore 214. The cover plate 260 is coupled to the low profile fusion plate 200 using a connecting pin 286 as shown in FIG. 12. The connecting pin 286 has a head 288 and a shaft 290. The head 288 has a lip 292 that abuts either the second face 264 or, if the cover plate bore 270 is countersunk, the shoulder 274. The shaft 290 has a proximal portion 294 proximate to the head 288, a distal portion 296 distal from the head 288, separated by a medial portion 298. The proximal portion 294 has a first thread $T_5$ that is designed to cooperatively engage the threads $T_4$ of the cover plate 260. The medial portion 298 is shown as being threadless and provides a transition from the proximal portion to the distal portion. The distal portion 296 has a second thread $T_6$ that is designed to cooperatively engage the threads $T_3$ of the inner threaded bore 234 of the connecting connector 224. The connecting pin 286 has length $L_4$ and couples the cover plate 260 to the low profile fusion plate 200.

Figure 13:
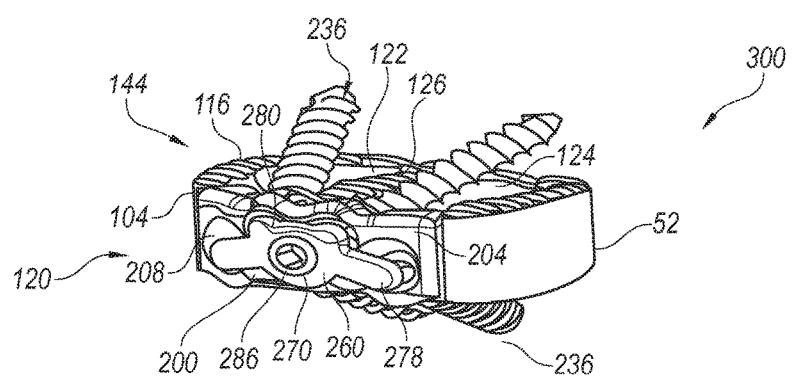
FIG. 13 is a perspective view of an implant consistent with the technology of the present application.

Referring now to FIG. 13, a low profile implant 300 consistent with the above is provided. The low profile implant 300 includes spacer 52 having the rearward portion 104 (or the anterior portion for the exemplary spinal application) voids 122 and 124 separated by a central strut 126. The protrusions 116 are shown on the top (or superior) portion. The cavity 120 in the rearward portion 104 has the low profile fusion plate 200 therein. The fastener bores 208 of the low profile fusion plate 200 are aligned, generally, with the spacer channels 144. The fasteners 236 extend through the fastener bores 208, spacer channels and extend out of the top portion and bottom portion of the spacer 52. The cover plate 260 is provided with arms 278 covering two of the fastener bores 208 and flared extensions 280 covering the other two of the fastener bores 208. The connecting pin 286 is then moved into cover plate bore 270. In a particular embodiment, the overall height of plate 200 (measured along the inferior to superior direction) is similar to or the same as the overall height of spacer 52. In this embodiment, implant 300 is a "zero profile" implant in that the plate 200 does not extend above or below the height of the disc space into which spacer 52 is disposed.

Figure 14:
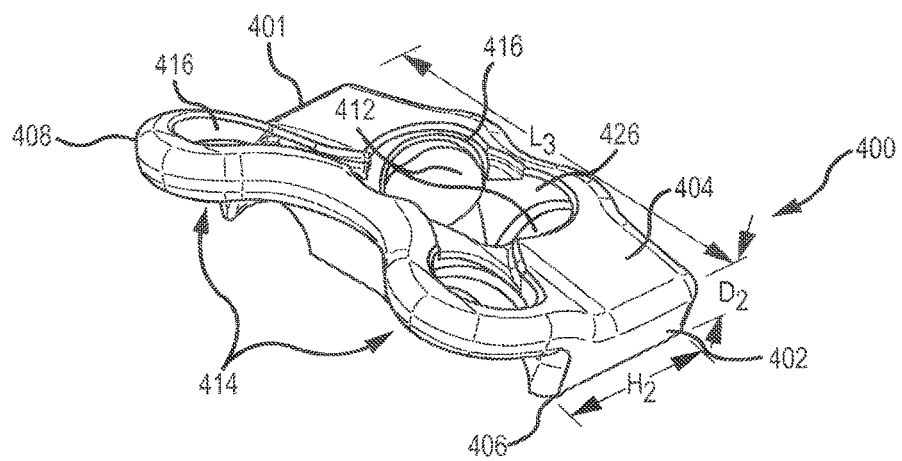
FIG. 14 is a perspective view of a fusion plate consistent with the technology of the present application.
Figure 15:
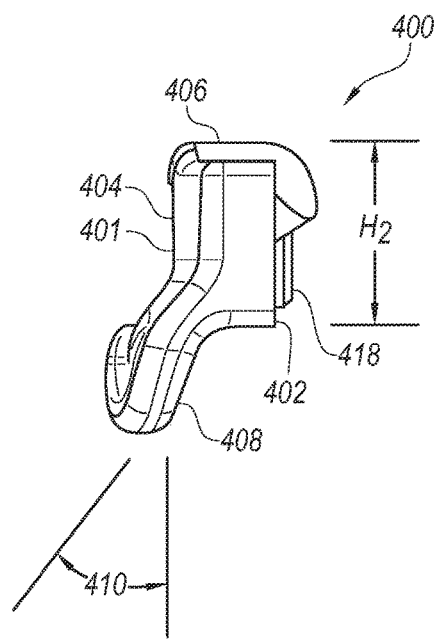
FIG. 15 is a side elevation view of the fusion plate of FIG. 14.

The low profile fusion plate 200 may not be usable in certain aspects or the technology. For example, the end plate or size of the vertebrae may not support a fastener in such a manner, the angle necessary to facilitate the fastener 236 extending from the rearward portion 104 through the top portion 106 or bottom portion 108 may not be possible, to name but two situations in which the tow profile construction as shown in FIG. 13 may not be possible or desirable. In these cases, it may be necessary to provide a fusion plate with a slightly higher profile than the low profile fusion plate 200, sometimes referred to as a middle profile fusion plate 400 or "single flange plate" as shown in FIGS. 14 and 15.

The middle profile fusion plate 400 has a main body portion 401 similar in construction to the low profile fusion plate 200 including a forward face 402 and a rearward face 404 opposite the forward face 402. A sidewall 406 extends between the forward face 402 and the rearward face 404. The edges of sidewall 406 may be beveled or chamfered to reduce trauma. The forward face 402 is generally sized to fit the cavity 120 of the spacer 52. Thus, the forward face 402 may have a length $L_3$, a height $H_2$, and a depth $D_2$ to allow middle profile fusion plate to cooperatively fit in cavity 120. The middle profile fusion plate 400 also has a first extension side 408 that extends from the main body portion 401 beyond the height $H_2$ in only one of the superior or inferior directions, which in this exemplary embodiment, is shown as extending in the inferior direction. A distal edge of the first extension side 408 may have a concave shape. The first extension side 408 has an angled forward face 402 and an angled rearward face 404. The first extension side 408 is angled at an angle 410 (shown in FIG. 15) with respect to the rearward face 404 to allow for the first extension side 408 to overlap one of the bones to be fused. The angle 410 provides that the portion of first extension side 408 distal from the rearward face 404 is offset from the spacer 52 rearward portion 104. While described as an angle for convenience, the first extension side 408 may have a slight curvature or sinusoidal shape rather than a straight angled surface. In a particular embodiment, the first extension side 408 is curved in a manner such that the distal tip portion of extension 408 is generally parallel to body portion 401.

As can be appreciated, the middle profile fusion plate 400 has a plurality of fastener bores 412 in the forward and rearward faces 402, 404 that cooperate with spacer channels in the implant to allow a set of fasteners to extend from the middle profile fusion plate 400 through the spacer 52 into the endplates of the associated vertebrae 40, 42. While the spacer could be Formed consistent with spacer 52 above, the spacer in this exemplary embodiment may be provided with spacer channels 144 on the upper edge 1-40 and no spacer channels 144 on the lower edge 142 as a design option.

A second plurality of fastener bores 414 are provided in the first extension side 408. The fastener bores 414 are arranged to allow the fastener 236 to extend through the angled forward face 402 and the angled rearward face 404 directly into, for example, a pedicle of the inferior vertebrae 42. The fastener bores 412, 414 have an internal sidewall 416 forming a concave surface for cooperative engagement with the convex lower surface 242 of head 238 of fastener 236. The middle profile fusion plate 400 includes a plate bore 418 similar to plate bore 214 to receive the threaded connector 224 that couples the middle profile fusion plate 400 to the spacer 52.

Figure 16:
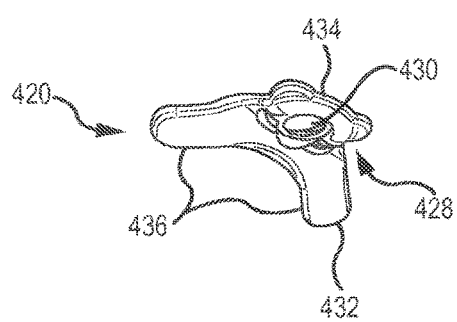
FIG. 16 is a perspective view of a cover plate consistent with the technology of the present application.
Figure 17:
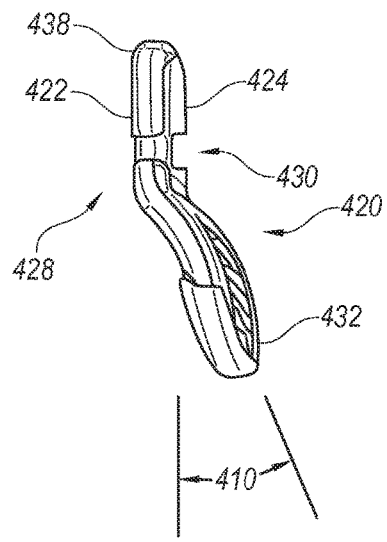
FIG. 17 is a side elevation view of the cover plate of FIG. 16.

Referring now to FIGS. 16 and 17, a perspective view and side elevation view of a middle profile cover plate 420 is shown. The cover plate 420 has a first face 422 and a second face 424 opposite the first face 422, which is similar to cover plate 260 described above. The cover plate 420 may be shaped to fit into a recess 426 in the middle profile fusion plate 400, as shown in FIG. 14. The cover plate 420, as shown, generally has a main body portion 428 with a cover plate bore 430, which may be constructed similar to cover plate bore 270 described above to receive the connecting pin 286 to couple the cover plate 420 to the middle profile fusion plate 400. The middle profile fusion plate 400 comprises a plurality of arms 432 extending at an angle 410 extending from main body portion 428 and a flared extension 434 extending from the main body portion 428. The arms 428 are angled to coincide with the angle 410 of the first extension side 408 such that the arms 432 extend over a portion of the fastener bores 414. The arms 432 may have a web of material (not shown) between them to form a flared extension instead of arms as a matter of design choice. Also, the arms 432 are designed to cooperatively engage the recess 426 and, as such, may have a curvature or sinusoidal shape.

The arms extend from the main body portion a sufficient distance such that at least a distal end 436 of the arm extends over fastener bores 414. The distal end 436 of the arm, thus, resists the ability of the fastener 236 to reverse thread from the implant. The flared extension(s) 434 extends from the main body portion a sufficient distance such that at least distal ends 438 of the flared extension(s) 434 extend over fastener bores 412. The distal ends 438, thus, resist the ability of the fasteners 236 to reverse thread from the implant As can be appreciated, the shape, size, and whether arms or flared extensions are associated with cover plate 420 depends in part on the shape and size of fusion plate 54 (shown in FIG. 1). The shape and size of the cover plate 420, specifically shown in FIGS. 16 and 17, is designed for use with the middle profile fusion plate 400 shown in FIGS. 14 and 15. Generally, arms on cover plate 432 are associated with a single fastener bore 414 and flared extension(s) 434 are associated with multiple fastener bores 412.

Figure 18:
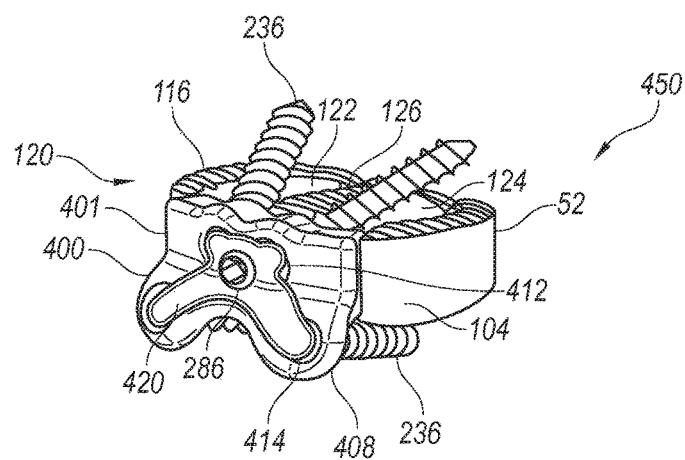
FIG. 18 is a perspective view of an implant consistent with the technology of the present application.

Referring now to FIG. 18, a middle profile implant 450 consistent with the above is provided. The middle profile implant 450 includes spacer 52 having the rearward portion 104 (or the anterior portion for the exemplary spinal application with voids 122 and 124 separated by a central strut 126. The protrusions 116 are shown on the top (or superior) portion. The cavity 120 in the rearward portion 104 has the middle profile fusion plate 400 therein. The fastener bores 412 of the middle profile fusion plate 400 are aligned, generally, with the spacer channels 144. The fasteners 236 extend through the fastener bores 412 and spacer channels and extend out of the top portion and bottom portion of the spacer 52. The fastener bores 414 in the first extension side 408 of the middle profile fusion plate 400 are aligned with the inferior vertebrae 42 in this example, but the fastener bores 414 may be aligned with the superior vertebrae 40 or other bone surfaces depending on the use. The fasteners 236 extend through the fastener bores 414 and into the pedicle or anterior side 46 of the inferior vertebrae 42. Depending on the dimensions, the fasteners 236 extending through the fastener bores 414 may not pass through spacer channels 144, and in those cases, the spacer channels may be removed. In a particular embodiment, the fasteners 236 extending through fastener bores 414 are generally parallel to spacer 52 surface. In this manner, fasteners 236 may be generally orthogonal to the bony surface to which they are coupled. In alternative embodiments, fasteners 236 extending through fastener bores 414 are at a diverging or converging angle relative to spacer 52 upper or lower surfaces. The cover plate 420 is provided with arms 432 covering two of the fastener bores 414 and flared extensions 434 covering the other two of the fastener bores 412. Generally, the arms 432 are associated with the bores on the first extension side and the flared extension is associated with the bores on the remainder of the fusion plate. The connecting pin 286 couples the cover plate 420 to the middle profile fusion plate 400.

Figure 19:
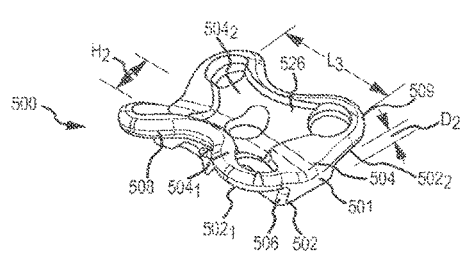
FIG. 19 is a perspective view of a fusion plate consistent with the technology of the present application.
Figure 20:
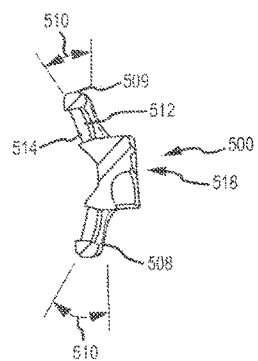
FIG. 20 is a side elevation view of the fusion plate of FIG. 19.

In some applications, the middle profile fusion plate 400 may not be usable for any number of reasons. In these cases, it may be necessary to provide a fusion plate with a slightly higher profile than the middle profile fusion plate 400, sometimes referred to as a high profile fusion plate 500 or "two flange plate" as shown in FIGS. 19 and 20. The high profile fusion plate 500 has a main body portion 501 similar in construction to the low profile fusion plate 200 including a forward face 502 and a rearward face 504 opposite the forward face 502. A sidewall 506 extends between the forward face 502 and the rearward face 504. The edges of sidewall 506 may be beveled or chamfered to reduce trauma. The forward face 502 is generally sized to fit the cavity 120 of the spacer 52. Thus, the forward face 502 may have a length $L_3$, a height $L_2$, and a depth $D_2$ to allow the high profile fusion plate to cooperatively engage cavity 120.

The high profile fusion plate 500 also has a first extension side 508 that extends beyond the height $F_{12}$ in one of the superior or inferior directions, which in this exemplary embodiment is shown as extending in the inferior direction and a second extension side 509. The first and second extension sides 508, 509 may be pinched such that a distal edge of the first and second extension sides 508, 509 has a concave shape. The first extension side 508 has an angled forward face $502_1$ and an angled rearward face $504_1$. The second extension side has an angled forward face $502_2$ and an angled rearward face $504_2$. The first extensions side 508 and the second extension side 509 are angled at an angle 510 with respect to the rearward face 504 to allow for each of the first and second extension sides 508, 509 to overlap opposite ones of the bones to be fused. The angle 510 provides that the portions of the first and second extension sides 508, 509 distal from the rearward face 504 are offset from the spacer 52 rearward portion 104. White described as an angle for convenience, the first and second extension sides 508, 509 may have a slight curvature or sinusoidal shape rather than a straight angled surface. One or both extension sides 508, 509 may have an orientation or curvature, and/or fastener bores similar to that described for extension side 408. Moreover, while described as symmetrical, the first extension side 508 and the second extension side 509 may be asymmetrical and may be necessarily so under certain anatomical conditions.

As can be appreciated, the high profile fusion plate 500 has a plurality of fastener bores 512 in the first and second extension sides 508, 509 that cooperate with a set of fasteners to extend from the high profile fusion plate 500 into the pedicle or anterior side of the associated vertebrae 40, 42. While the spacer could be formed consistent with spacer 52 above, the spacer in this exemplary embodiment may be provided without spacer channels 144 on the upper and lower edges 140, 142 as a design option. The fastener bores 512 have an internal sidewall 514 forming a concave surface for cooperative engagement with the convex lower surface 242 of head 238 of fastener 236. The high profile fusion plate 500 includes a plate bore 518 similar to plate bore 214 to receive the threaded connector 224 that couples the high profile plate 500 to the spacer 52.

Figure 21:
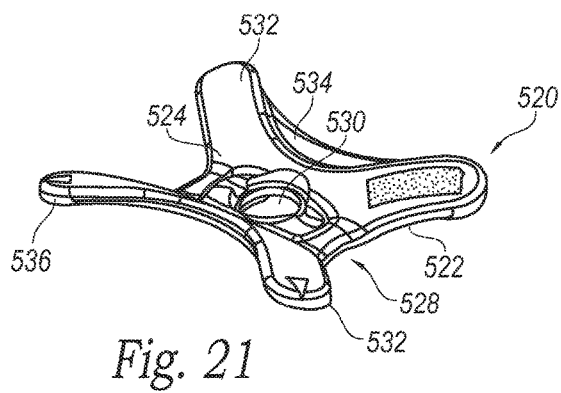
FIG. 21 is a perspective view of a cover plate consistent with the technology of the present application.
Figure 22:
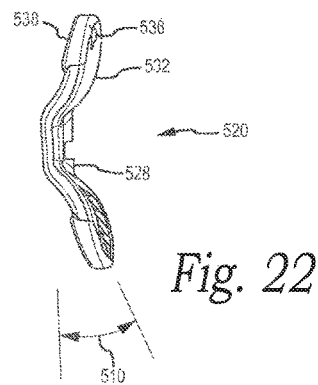
FIG. 22 is a side elevation view of the cover plate of FIG. 21.

Referring now to FIGS. 21 and 22, a perspective view and side elevation view of a high profile cover plate 520 is shown. The cover plate 520 has a first face 522 and a second face 524 opposite the first face 522, which is similar to cover plates 260, 420 described above. The cover plate 520 may be shaped to fit into a recess 526 in the fusion plate 500, as shown in FIG. 19. The cover plate 520, as shown, generally has a main body portion 528 with a cover plate bore 530, which is may be constructed similar to cover plate bore 270, 430 described above to receive the connecting pin 286 to couple the cover plate 520 to the high profile fusion plate 500.

The cover plate 520 comprises a plurality of arms 532 extending at an angle 510 extending from main body portion 528. The arms 532 are angled to coincide with the angle 510 of the first and second extension sides 508, 509 such that the arms 532 extend over a portion of the fastener bore 512. The arms 532 may have a web of material 534 there between. The web of material 534 may be extended from a flared extension instead of arms as a matter of design choice. Also, the arms 532 are designed to cooperatively engage the recess 526 and, as such, may have a curvature or sinusoidal shape. The arms extend from the main body portion a sufficient distance such that at least a distal end 536 of the arm extends over fastener bores 512. The distal end 536 of the arm, thus, resists the ability of the fastener 236 to reverse thread from the implant. As shown in FIGS. 21 and 22, the distal end 536 of the arms 532 may have pads 538 that extend from the arms 532 into the fastener bores 512 to contact the fastener heads 238. The pads 538 shown herein may be provided on any of the arms or flared extensions described above.

As can be appreciated, the shape, size, and whether arms or flared extensions are associated with cover plate 520 depends in part on the shape and size or fusion plate 54 (shown in FIG. 1). The shape and size of the cover plate 520, specifically shown in FIGS. 21 and 22, is designed for use with the high profile fusion plate 500 shown in FIGS. 19 and 20. Generally, arms on cover plate 520 are associated with a single fastener bore 512 and flared extension(s) having the web of material 534 may be associated with multiple fastener bores 512.

Figure 23:
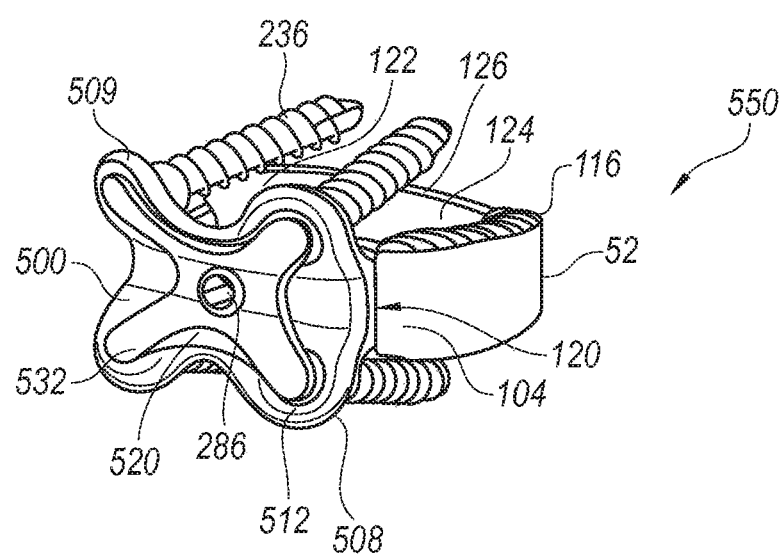
FIG. 23 is a perspective view of an implant consistent with the technology of the present application.
Figure 24:
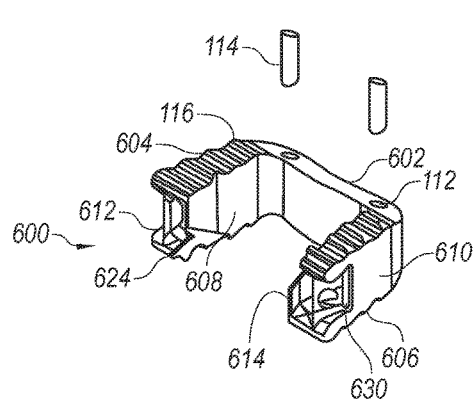
FIG. 24 is a perspective view of a spacer consistent with the technology of the present application.

Referring now to FIG. 23, a high profile implant 550 consistent with the above is provided. The high profile implant 550 includes spacer 52 having the rearward portion 104 (or the anterior portion for the exemplary spinal application) with voids 122 and 124 separated by a central strut 126. The protrusions 116 are shown on the top (or superior) portion. The cavity 120 in the rearward portion 104 has the high profile fusion plate 500 therein. The fastener bores 512 in the first and second extension sides 508, 509 of the high profile fusion plate 500 are aligned with the pedicle or the anterior sides of the inferior and superior vertebrae 42, 40 in this example, but the fastener bores 512 may be aligned with other bone surfaces depending on the use. The fasteners 236 extend through the fastener bores 512 and into the pedicle or anterior side 46 of the superior and inferior vertebrae 40, 42. Depending on the dimensions, the fasteners 236 extending through the fastener bores 512 may not pass through spacer channels 144, and in those cases, the spacer channels may be removed. Fasteners 236 may be generally orthogonal to anterior sides 46 of vertebrae 40, 42, or may alternatively enter the vertebrae at divergent or convergent angles in one or more planes. The cover plate 520 is provided with arms 532 covering the fastener bores 512. The connecting pin 286 couples the cover plate 520 to the high profile fusion plate 500.

The low, middle, and high profile fusion plates 200, 400, and 500 have heretofore been described with respect to the spacer 52. The spacer 52 in this exemplary embodiment comprises a plurality of voids 122, 124 and a central strut 126. For any number of reasons, a surgeon may be desirous of a spacer with a single void instead of a plurality of voids 122, 124 separated by the central strut 126. In this case, a spacer 600 is provided. FIGS. 24-27 show a perspective, plan (superior to inferior direction), side (lateral), and rearward view (anterior to posterior direction) of the spacer 600. The spacer 600 is generally shaped to fit within the intervertebral space, and as can be appreciated, generally resides around a perimeter of the space. The spacer 600 includes a forward portion 602, which may be referred to as a posterior portion 602, a top portion 604, which may be referred to as a superior portion 604, a bottom portion 606, which may be referred to as an inferior portion 606, a first arm 608, and a second arm 610. The first and second arms 608, 610 extend in a rearward (or anterior) direction and terminate at first and second anterior ends 612, 614 respectively. Similar to spacer 52, spacer 600 may include apertures 112 to receive radio opaque plugs 114. The posterior portion 602, the first arm 608, and the second are 610 define a void 616. The void 616 may be packed with material to facilitate bone growth and fusion. The anterior portion or rearward portion of the spacer is generally open between the first and second arms 608, 610. A length $L_{11}$ is provided such that the spacer is approximately sized to fit about the perimeter of the intervertebral disc space. In a particular embodiment, spacer 600 has an overall outer shape that generally conforms to the outer shape of a cervical vertebra, or more specifically, to the shape of an endplate of the cervical vertebra.

Figure 25:
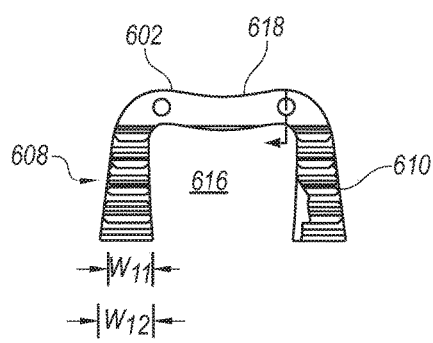
FIG. 25 is a top plan view of the spacer of FIG. 24.
Figure 26:
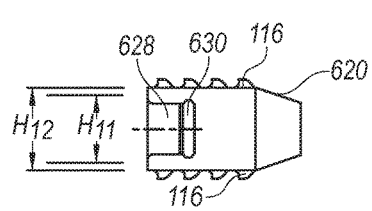
FIG. 26 is a side elevation view of the spacer of FIG. 24.
Figure 27:
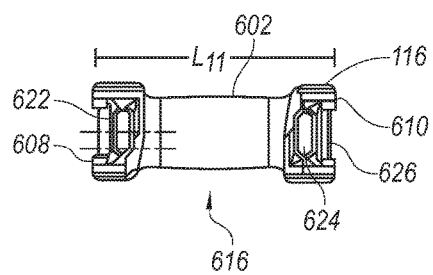
FIG. 27 is a rearward elevation view of the spacer of FIG. 24.

As shown in FIG. 25, the forward portion 602 may be shaped to provide a convex, concave, and convex portion forming a recess 618. The recess 618 is configured to avoid the dura in spinal applications. The arms 608, 610 have a width it where they connect to the forward portion 602. The arms may provide for a constant width or, as shown in the exemplary embodiment, the width may taper to a width $W_{12}$ at the first and second anterior ends 612, 614 (which may be referred to as the anterior ends). The width $W_{12}$ is greater than the width $W_{11}$ when the arms taper. The first and second arms 608, 610 may have protrusions 116 on the top portion 604, the bottom portion 606, or a combination thereof. The forward portion 602 may include protrusions 116, but typically does not have protrusions to facilitate insertion of the spacer 600 to the intervertebral disc space. Further, as shown in FIG. 26, the forward portion 602 may have a tapered portion 620 to facilitate insertion of the spacer as well. The first and second arms 608, 610 may have a constant height $H_{11}$ or, as shown in the exemplary embodiment, the side portions may expand in height in the rearward (anterior) direction to a second height $H_{12}$. The height $H_{11}$ and height $H_{12}$ are generally selected by the surgeon to provide the desired spacing between the vertebral bodies.

The first and second anterior ends 612, 614 have a rearward facing surface 622 with a blind hole 624. The blind hole 624 is used in conjunction with an alignment tab or pin on the fusion plates, which will be explained further below. The first and second arms 608, 610 also include side pockets 626 on the respective lateral sides. The side pockets 626 are formed by a cut-out in the lateral side terminating in a ramped medial wall 628 separating the blind hole 624 and the side pocket. The side pocket 626 has an indentation 630 at the end of the side pocket. The ramp medial wall 628 forms a wedge in the medial to lateral direction away from the void 616. The ramp medial wall 628 forces a corresponding spring arm on the fusion plates, which will be explained further below, elastically outward. The spring arms terminate in a flange that operatively engages the indentation 630. The flange is biased into the indentation by the elastic deformation of the spring arms forming a snap-lock between the fusion plate and the spacer 600.

Figure 28:
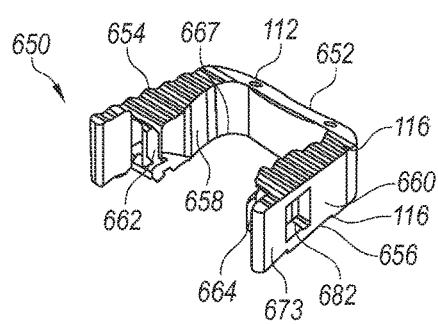
FIG. 28 is a perspective view of a spacer consistent with the technology of the present application.
Figure 29:
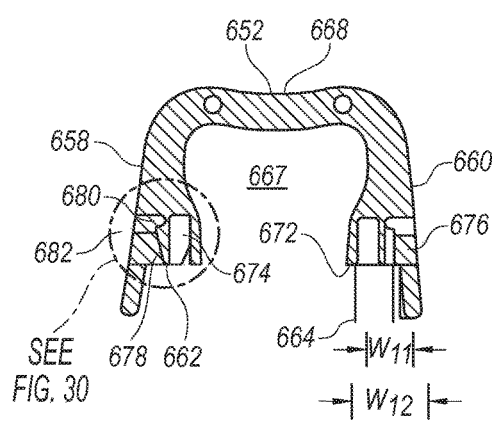
FIG. 29 is a top plan view of the spacer of FIG. 28
Figure 30:
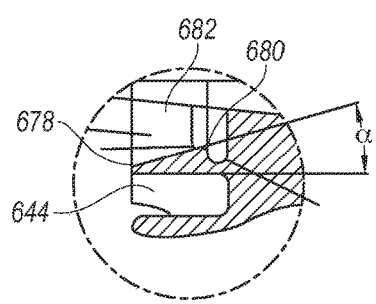
FIG. 30 is an enlarged view of a portion of the spacer of FIG. 29.

With reference now to FIGS. 28-30, a spacer 650 consistent with the technology of the sent application is shown. The spacer 650 is generally similar to the spacer 600 and includes a forward portion 652, which may be referred to as a posterior portion 652, a top portion 654, which may be referred to as a superior portion 654, a bottom portion 656, which may be referred to as an inferior portion 656, a first arm 658, and a second arm 660. The first and second arms 658, 660 extend in a rearward (or anterior) direction and terminate at first and second anterior ends 662, 664 respectively. Similar to spacer 600, spacer 650 may include apertures 112 to receive radio opaque plugs (not specifically shown in FIGS. 28-30). The posterior portion 652, the first arm 658, and the arm 660 define a void 667. The void 667 may be packed with material to facilitate bone growth and fusion.

As shown in FIG. 29, the forward portion 652 may be shaped to provide a convex, concave, and convex portion forming a recess 668. The recess 668 is configured to avoid the dura in spinal applications. The arms 658, 660 have a width $W_{11}$ where they connect to the forward portion 652. The arms may provide for a constant width or, as shown in the exemplary embodiment, the width may expand to a width $W_{12}$ at the first and second anterior ends 662, 664. Rather than a constant expansion, as shown with spacer 600, spacer 650 provides arms 658, 660 with a curved interior wall. The width $W_{12}$ is greater than the width $W_{11}$ in this exemplary embodiment. The first and second arms 658, 660 may have protrusions 116 on the top portion 651, the bottom portion 656, or a combination thereof. The forward portion 652 may include protrusions 116, but typically does not have protrusions to facilitate insertion of the spacer 650 to the intervertebral disc space.

The first and second anterior ends 662, 664 have a rearward facing surface 672 with a blind hole 674. The first and second anterior ends 662, 664 further have a lateral, flared wall extension 673. The blind hole 674 is used in conjunction with an alignment tab or pin on the fusion plates, which will be explained further below. The first and second arms 658, 660 also include side pockets 676 on the respective lateral sides, which are shown in more detail in FIG. 30. The side pockets 676 are formed by a cut-out in the lateral side terminating in a ramped medial wall 678 separating the blind hole 674 and the side pocket 676. The side pocket 676 has an indentation 680 at the end of the side pocket. The ramp medial wall 678 forms a wedge diverging at an angle a in the medial to lateral direction away from the void 667. The ramp medial wall 678 forces a corresponding spring arm on the fusion plates, which will be explained further below, elastically outward. The spring arms terminate in a flange that operatively engages the indentation 680. The flange is biased into the indentation by the elastic deformation of the spring arms forming a snap-lock between the fusion plate and the spacer 650. The first and second arms further have a window 682 about the side pockets 676 to facilitate a tool. The tool may be to release the snap-lock, for example, among other things.

The spacers 600 and 650 have a similar connection to a low, medium, and high profile fusion plates 700, 750, and 800 that will now be described with reference to the FIGS. 31-37. The connection between the low, medium, and high profile fusion plates and the spacers is similar, and will only be described herein in connection with the low profile fusion plate 700.

Figure 31:
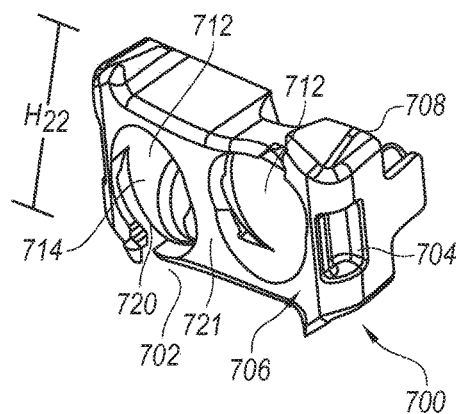
FIG. 31 is a perspective view of a fusion plate consistent with the technology of the present application.
Figure 32:
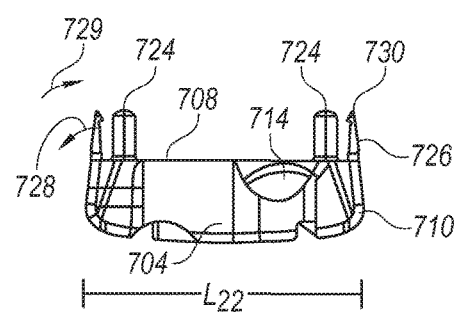
FIG. 32 is a top plan view of the fusion plate of FIG. 31.
Figure 33:
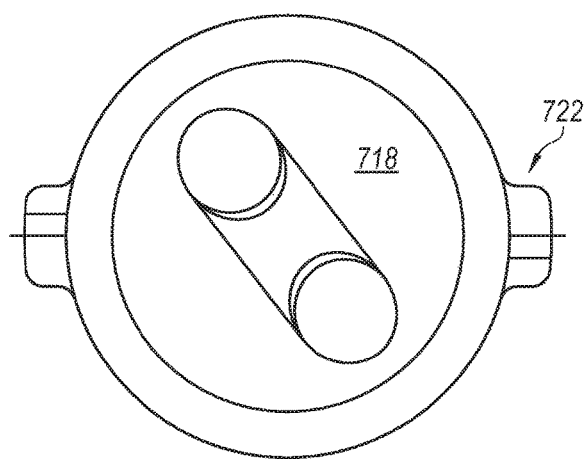
FIG. 33 is a top plan view of a lock consistent with the technology of the present application.
Figure 34:
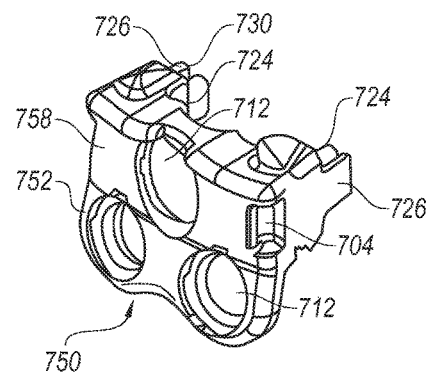
FIG. 34 is a perspective view of a fusion plate consistent with the technology of the present application.
Figure 35:
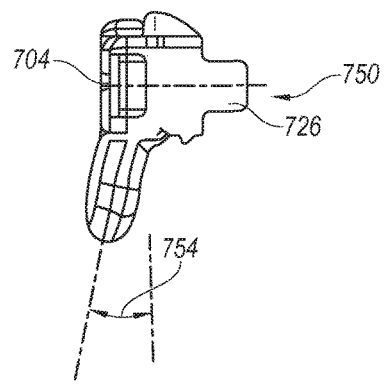
FIG. 35 is a side elevation view of the fusion plate of FIG. 34.

With reference to FIGS. 31 and 32, a low profile fusion plate 700 is shown. The low profile fusion plate 700 generally has a main body portion 701 with a height $H_{22}$ and a length $L_{22}$. The height $H_{22}$ and the length $L_{22}$ are substantially equal to the height $H_{11}$ and/or $H_{12}$ and the length $L_{11}$ of the spacer. The low profile fusion plate 700 may have a cut-out 702 on the superior and inferior portions of the plate 700 to provide access to the void 667. The plate 700 includes side cut-outs 704 to allow a tool to grip the plate 700 for connection to the spacer 600, 605.

As can be appreciated, the low profile fusion plate 700 includes a rearward facing (or anterior facing) surface 706 and a forward facing (or posterior facing) surface 708 opposite the rearward facing surface 706. A sidewall 710 extends between the rearward, and forward facing surfaces 706, 708. The plate 700 further includes a plurality (in this exemplary embodiment two (2)) fastener bores 712. The fastener bores extend from the rearward facing surface 706 to the forward facing surface 708. The fastener bores have an internal sidewall 714 forming a concave surface. For cooperative engagement with a fastener, such as fasteners 236 (FIG. 9). Generally, one fastener would extend from the low profile fusion plate 700 to the superior endplate 55 and one fastener would extend from the low profile fusion plate 700 to the inferior endplate 5.

The fasteners 236 may be inhibited from reverse threading using a bushing or a cover plate as described above. As shown, however, the low profile fusion plate may provide for a lock associated with each bore, such as, for example, a cap 718 (FIG. 33) that fits into a groove 720. The cap has a tab 722 extending from the cap 718 that fits into the groove 720 to inhibit reverse threading of the fasteners. The cap and plate are further described in U.S. patent application Ser. No. 12/404,051, titled Spinal Plate Assemblies with Backout Protection Cap and Methods, which published on Sep. 16, 2010, under publication number 2010/0234897 A1, and is incorporated herein by reference as if set out in full.

The low profile fusion plate 700 includes a pair of alignment protrusions 724 extending in a forward (posterior) direction from the forward facing surface 708. The alignment protrusions 724 are sized to cooperatively engage the blind holes 624, 674 in the spacers 600, 650. Arranged laterally outwardly from the alignment protrusions 724 are locking protrusions 726. The locking protrusions 726 are elastic and can be biased by forcing the protrusion 726 to bend in the direction shown by arrow 728. The locking protrusion 726 ends in a hook 730 sized to operationally engage the indentation 630, 680. In an alternative embodiment, fusion plate 700 uses only locking protrusions 726 to engage and couple to spacers 600, 650.

In operation, the spacer 600, 650 would be implanted to the intervertebral disc space. The surgeon would align the alignment protrusions 724 with the blind holes 624, 674 in the spacer. The surgeon would next push the alignment protrusions 724 into the blind holes 624, 674. The locking protrusions 726 would align with side pockets 626, 676. As the low profile fusion plate 700 is pushed onto the spacer 600, 650, the ramp medial wall 628, 678 would elastically bias the locking protrusions in a direction 728 until the hooks 730 engaged the indentations 630, 680. The locking protrusion 726 would return as shown by the arrow 729 such that the hooks 730 and indentations 630, 680 form a snap lock coupling the spacer 600, 650 with the low profile fusion plate 700. Alternatively, the engagement between spacer 600, 650 and plate 700 occurs prior to implantation in the intervertebral disc space. In this embodiment, the two components are coupled together and then inserted as a single element in the patient. Additionally, bone growth promoting substances may be placed in the spacer 600, 650 prior to, during, or after implantation of spacer 600, 650 within the disc space.

With reference to FIGS. 34-37, a medium profile fusion plate 750 and a high profile fusion plate 800 are provided. The medium profile fusion plate 750 and high profile fusion plate 800 couple to the spacer in a manner similar to the low profile fusion plate 700, so those similarities will not be re-explained herein. The medium profile fusion plate 750 has a first extension side 752 that extends in either the superior or inferior direction to overlap with a portion of the vertebral body. The first extension side is flared at an angle 754 to accommodate the anatomy of the patient. The first extension side 752 further includes at least one fastener bore 712 to allow fasteners to be implanted to the vertebral body through the first extension side 752. The main body portion 758 may have one central fastener bore 712 as shown or a plurality of fastener bores 712 as shown above with respect to the low profile fusion plate 700. In some embodiments, a portion of first side extension or flange 752 is flared at an angle 754 adjacent the engagement to spacer 600, 650, and then includes a curved portion of first side extension. In this manner, the first side extension 752 may angle away from bony anatomy, and the curved portion adjusts the angle of the fastener bores 712 relative to the vertebra. For example, for an implant placed from the anterior side of a patient, the first side extension 752 is angled first in an anterior direction, and then has a curved portion which places bores 712 in a position generally parallel to the anterior face of the vertebra. This arrangement would allow fasteners to be inserted, for example, parallel to one another and generally perpendicular to the anterior face of the vertebra. High profile fusion plate 800 includes the first extension side 752 as well as a second extension side 802 such that side extensions extend in both the superior and inferior direction to overlap portions of the adjacent vertebral bodies. The high profile fusion plate 800 has at least one fastener bore 712 in each of the first and second extensions side 752, 802. Additionally, the main body portion 804 of the high profile fusion plate 800 may not have any fastener bores.

Figure 38:
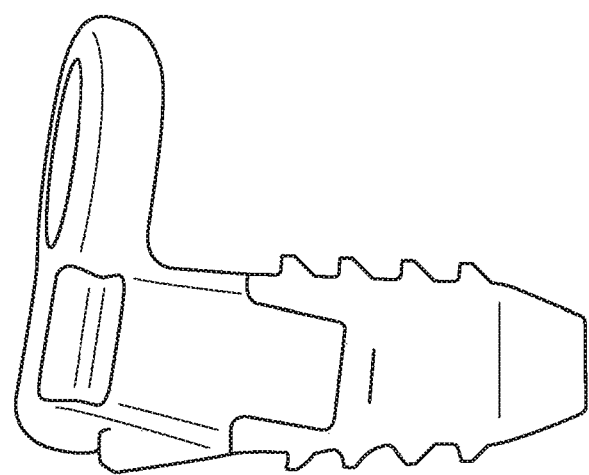
FIGS. 38-40 are side elevation views of alternative fusion plates coupled to a spacer using an angled engagement feature.
Figure 39:
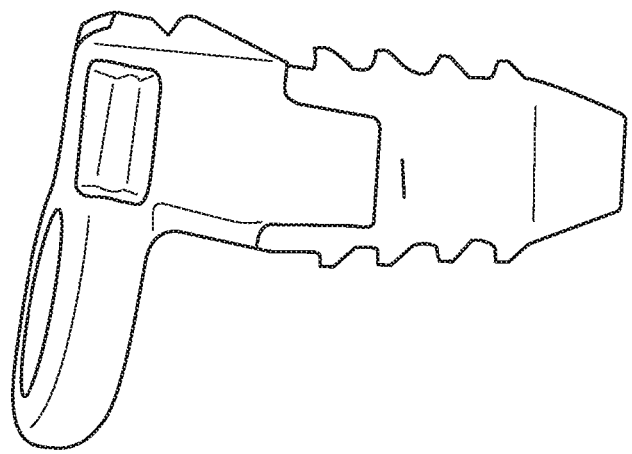
Figure 40:
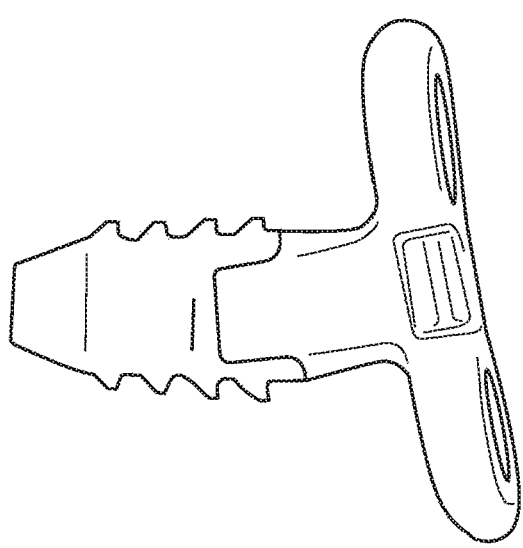

In alternative embodiments, locking protrusion 726 and/or alignment protrusions 724 are disposed at an angle relative to main body portion 758. In one such embodiment the medium profile fusion plate 750 has this angled relationship. In this manner, the angle between first side extension 752 and the spacer 600, 650 will depend on the orientation of the two components when coupled. In one orientation, the coupling of plate 750 and spacer 600 produces an acute angle between first side extension 752 and spacer 600. In the opposite orientation (filmed upside down or 180 degrees), the coupling of plate 750 and spacer 600 produces an obtuse angle between the first side extension 752 and spacer 600. In still another embodiment as shown in FIGS. 38-40, the blind holes 624, 674 and/or side pockets 626, 676 in spacer 600, 650 provide the angled relationship between the spacer and the plate.

Figure 36:
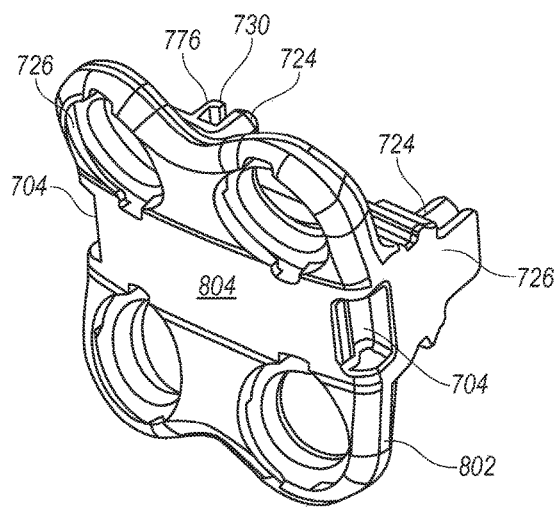
FIG. 36 is a perspective view of a fusion plate consistent with the technology of the present application.
Figure 37:
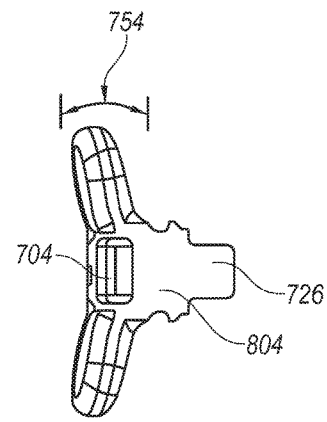
FIG. 37 is a side elevation view of the fusion plate of FIG. 36.
Figure 41:
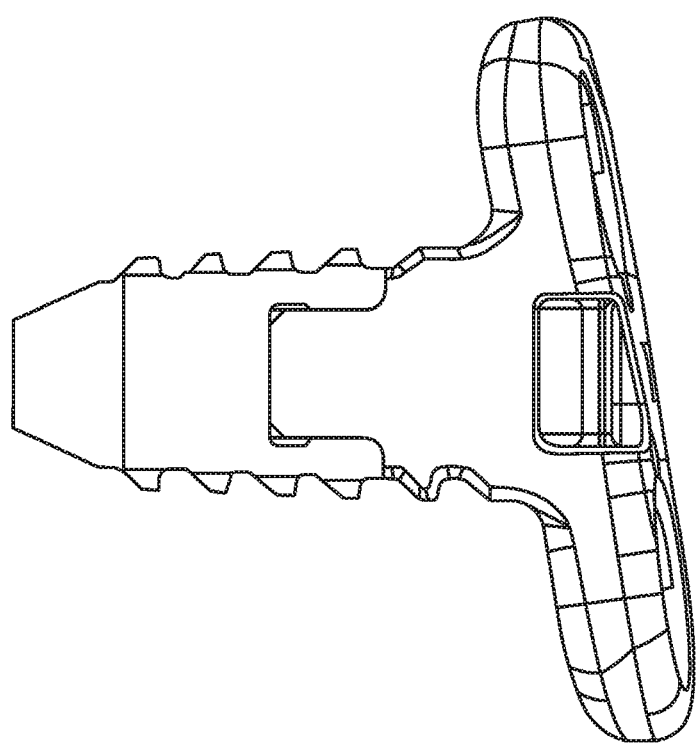
FIGS. 41-42 are side and perspective views of an alternative implant showing a fusion plate with an alternative angled engagement with the spacer.
Figure 42:
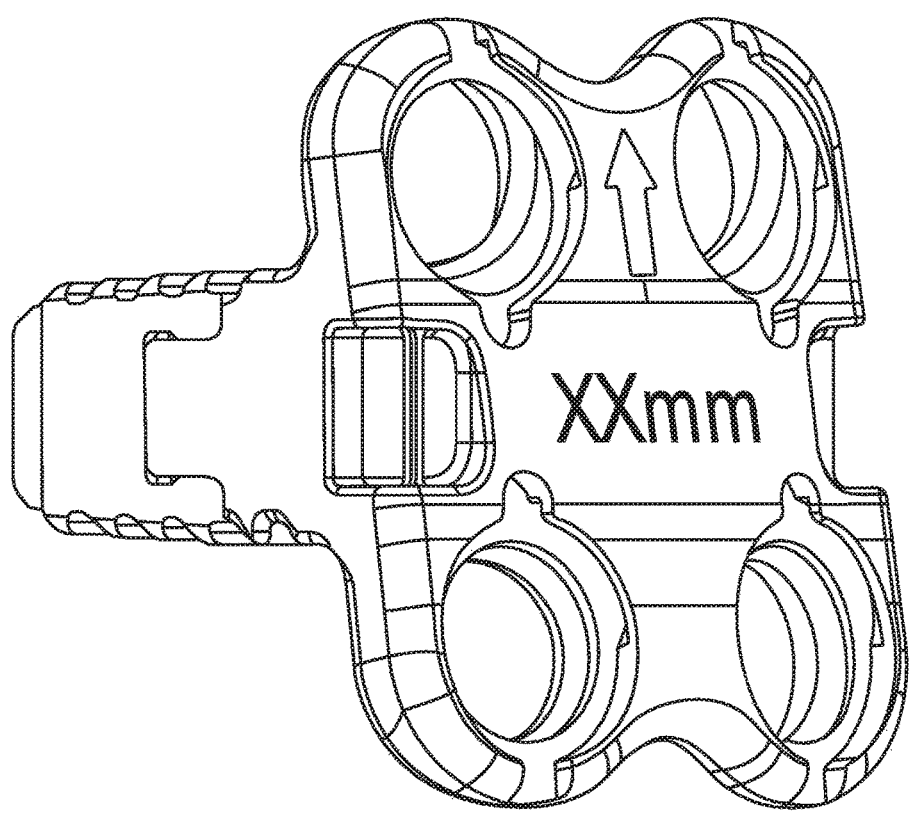

The high profile fusion plate 800, or two-flange plate 800, is depicted in FIGS. 36-37 as having a same angle 754 for both the first side extension 752 and the second side extension 802. In an alternative embodiment, the angle 754 is different for the two side extensions. For example, in some cases angle 754 may be smaller or greater for the second side extension 802 than it is for first side extension 752. In some cases, angle 754 is zero (0) degrees for one or both side extensions 752, 802. In still another embodiment, such as that shown in FIGS. 41-42, the first and second side extensions 752, 802 are generally coplanar, but have different angles 754 between the side extension and the spacer 600 or between the side extension and the plate main body portion 758.

Notice that the above described implant was described with reference to a low profile fusion plate, a middle profile fusion plate, and a high profile fusion plate. On reading the disclosure, one of ordinary skill in the art will now recognize that the use of low profile, middle profile, and high profile are relative terms to distinguish the above described embodiments and are provided for reference and should not be construed to limit the technology of the present application.

The technology of the present application also includes methods for implanting the apparatus described above. White the methodology is provided in certain discrete steps, one of ordinary skill in the art will recognize that the steps identified may be broken into multiple steps or multiple steps may be combined into a single step. Moreover, the sequence of events provided may be altered or rearranged without departing from the technology of the present application. With that in mind, the surgeon would first determine the appropriate spacer to be used. In spinal applications, the spacer may be sized to restore the height corresponding to the height of a healthy vertebra. In other applications, the spacer may be sized to most readily promote fusion or the like.

Once the appropriate spacer is identified, the threaded connector may be threaded into the spacer bore, although the threaded connector may already be threaded to the spacer. The surgeon would next implant the spacer and threaded connector to the fusion site. Notice the threaded connector may be threaded when the spacer is in the fusion site as a matter of surgical technique. Next the surgeon would determine whether a low, middle, or high profile fusion plate is appropriate for the patient's anatomy. The fusion plate would be coupled to the threaded connector. For example, the protrusions on the slotted head may be compressed and fitted into the fusion bore until a snap fit is formed between the slotted head and the fusion plate.

The fusion plate may be fitted to the threaded connector such that the spacer and fusion plate are placed at the fusion site at the same time.

The surgeon would next use fasteners to couple the implant to the honey segments, such as the superior and inferior vertebrae for a spinal application. Finally, a cover plate that corresponds to the fusion plate is selected and coupled to the fusion plate. For example, the connecting pin may be threaded through the cover plate bore and fusion plate bore into the interval threads of the threaded connector to couple the cover plate, fusion plate, and spacer.

The implant may be supplemented with bone growth promoting substances to facilitate fusion of adjacent vertebrae between spinous processes, laminae, transverse processes, facets, and/or other spinal structures. The bone growth promoting substances may be spaced from the implant, placed adjacent the implant, sandwiched between the implant and underlying bone, placed inside the implant, coated onto the implant, and/or otherwise placed relative to the implant. If it is coated onto the implant, it may cover the entire implant or only selected portions of the implant such as the extensions, fasteners, spinous process contacting portions of the spacer, and/or other portions.

As used herein, bone growth promoting substances may include bone paste, bone chips, bone strips, structural bone grafts, platelet derived growth factors, bone marrow aspirate, stem cells, bone growth proteins, bone growth peptides, bone attachment proteins, bone attachment peptides, hydroxylapatite, calcium phosphate, other suitable bone growth promoting substances, and/or combinations thereof.

The implant and any associated cerclage or other components may be made of any suitable biocompatible material eluding among others metals, resorbable ceramics, non-resorbable ceramics, resorbable polymers, and non-resorbable polymers. Some specific examples include stainless steel, titanium and its alloys including nickel-titanium alloys, tantalum, hydroxylapatite, calcium phosphate, bone, zirconia, alumina, carbon, bioglass, polyesters, polylactic acid, polyglycolic acid, polyolefins, polyamides, polyimides, polyacrylates, polyketones, fluoropolymers, and/or other suitable biocompatible materials and combinations thereof.

Various methods, systems and devices for treating spinal fractures are disclosed. While detailed descriptions of one or more embodiments have been provided above, various alternatives, modifications, and equivalents are possible. Therefore, the above description should not be taken as limiting the scope of possible embodiments, which is defined by the appended claims.

What is claimed is:

1. An implant configured to be interposed between opposing faces of two bones to be fused together, the implant comprising:
    a spacer configured to fit between the opposing faces of the two bones to promote fusion of the two bones, the spacer having a forward portion with a first end and a second end opposite the first end, a first arm having an exterior lateral surface positioned toward the first end and extending in a rearward direction to terminate at a first anterior end, a second arm having an exterior lateral surface positioned toward the second end and extending in the rearward direction to terminate at a second anterior end, a hole in at least one of the first or second anterior ends, and a side pocket in the exterior lateral surface of at least one of the first or second arms; and
    a fusion plate sized to extend from the first rearward facing surface to the second rearward facing surface, the fusion plate having a forward facing surface comprising at least one alignment tab slidable into the at least one hole and at least one lock tab releasably coupled to the at least one side pocket, the fusion plate having at least two throughbores configured to receive at least two bone fasteners,
    wherein one of the bone fasteners is adapted to couple the fusion plate to a first of the opposing bones and the other of the bone fasteners is adapted to couple the fusion plate to a second of the opposing bones.

2. The implant of claim 1, further comprising at least one lock coupled to the fusion plate and adapted to prevent at least one of the bone fasteners from reverse threading.

3. The implant of claim 2, wherein the at least one lock comprises a cover plate.

4. The implant of claim 2, wherein the at least one lock comprises a cap releasably coupled to each of the at least two throughbores.

5. The implant of claim 1, wherein the fusion plate comprises a main body portion and a first extension side portion, the main body portion comprising a forward face, a rearward face opposed to the forward face, and a sidewall connecting the forward face and the rearward face, the main body portion sized to substantially fit between the opposing faces, the first extension side portion configured to extend beyond at least one of the top portion or the bottom portion of the spacer.

6. The implant of claim 5, wherein the first extension side portion is positioned transverse to the main body portion.

7. The implant of claim 5, wherein the first extension side portion has a curved portion.

8. The implant of claim 5, wherein the first extension side portion defines a flange.

9. The implant of claim 5, wherein the fusion plate further comprises at least a second extension side portion opposite the first extension side portion and configured to extend beyond the other of the top portion or the bottom portion of the spacer.

10. The implant of claim 9, wherein the second extension side portion is positioned transverse to the main body portion.

11. The implant of claim 10, wherein the first and second extension side portions are disposed at different angles relative to the main body portion.

12. The implant of claim 1, further comprising a plurality of wall extensions extending from the first and second anterior ends in a rearward direction.

13. The implant of claim 12, wherein the exterior lateral surface comprises at least one window adapted to provide access to the at least one side pocket.

14. The implant of claim 1, wherein the forward portion, first arm, and second arm define a void.

15. The implant of claim 1, wherein the hole comprises at least one hole in the first anterior end and at least one hole in the second anterior end.

16. The implant of claim 1, wherein the at least one side pocket comprises at least one side pocket in the first arm and at least one side pocket in the second arm.

17. The implant of claim 1, wherein the side pocket is formed by a cut-out in the exterior lateral surface.

18. The implant of claim 1, wherein the side pocket and the hole are on the same arm.

19. The implant of claim 1, wherein the side pocket comprises a ramp medial wall expanding in a forward direction.

20. The implant of claim 19, wherein the ramp medial wall biases the lock tab.

21. The implant of claim 1, wherein the side pocket terminates with an indentation and wherein the lock tab terminates in a hook side to operationally engage the indentation forming a snap-lock.

* * * * *